US012325688B2

(12) United States Patent
Moaddel et al.

(10) Patent No.: US 12,325,688 B2
(45) Date of Patent: Jun. 10, 2025

(54) GINGERENONE A PRODRUGS AS SENSOTHERAPEUTICS AND METHODS OF USE

(71) Applicant: The U.S.A., as Represented by the Secretary, Department of Health and Human Services, Bethesda, MD (US)

(72) Inventors: Ruin Moaddel, Bel Air, MD (US); Luigi Ferrucci, Baltimore, MD (US); Kotb Abdelmohsen, Nottingham, MD (US); Myriam Gorospe, Elliot City, MD (US); Martina Rossi, Baltimore, MD (US); Christopher E. Ramsden, Bethesda, MD (US); Gregory S. Keyes, Timonium, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/832,248

(22) PCT Filed: Jan. 17, 2023

(86) PCT No.: PCT/US2023/010962

§ 371 (c)(1),
(2) Date: Jul. 23, 2024

(87) PCT Pub. No.: WO2023/146771

PCT Pub. Date: Aug. 3, 2023

(65) Prior Publication Data

US 2025/0115543 A1 Apr. 10, 2025

Related U.S. Application Data

(60) Provisional application No. 63/302,873, filed on Jan. 25, 2022.

(51) Int. Cl.
*C07C 69/587* (2006.01)
*A61K 31/232* (2006.01)
(Continued)

(52) U.S. Cl.
CPC .......... *C07C 69/587* (2013.01); *A61K 31/232* (2013.01); *A61P 39/00* (2018.01); *C07C 229/38* (2013.01)

(58) Field of Classification Search
CPC ..... A61K 31/232; A61K 47/542; A61P 25/28; A61P 35/00; A61P 9/10; C07C 69/587
See application file for complete search history.

(56) References Cited

U.S. PATENT DOCUMENTS

2016/0074338 A1   3/2016   Lee et al.

OTHER PUBLICATIONS

Bieber, "Atopic dermatitis: an expanding therapeutic pipeline for a complex disease," *Nature Reviews*, vol. 21, Jan. 2022, pp. 21-40.
(Continued)

*Primary Examiner* — Savitha M Rao
(74) *Attorney, Agent, or Firm* — Klarquist Sparkman, LLP

(57) ABSTRACT

Gingerenone A prodrug compounds have a structure according to Formula I, or a pharmaceutically acceptable salt thereof wherein one of $R^1$ and $R^2$ is H or —C(O)—R and the other of $R^1$ and $R^2$ is —C(O)—R. Each R independently is $R^A$ or, where $R^A$ is $C_{18}$-$C_{22}$ alkenyl, and $R^B$ is an amino acid side chain. The compounds are useful for inhibiting or eliminating senescence. The compounds may be administered to a subject having a senescence-associated disease or disorder, neuroinflammation, pain, and/or an amino acid deficiency.

(I)

(Continued)

-continued

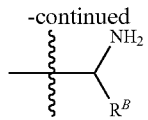

13 Claims, 22 Drawing Sheets

(51) Int. Cl.
*A61P 39/00* (2006.01)
*C07C 229/38* (2006.01)

(56) References Cited

OTHER PUBLICATIONS

International Search Report and Written Opinion for International Application No. PCT/US2023/010962, mailed Apr. 28, 2023, 13 pages.

Mirrahimi, et al., "Evaluating the Effect of Eicosapentaenoic Acid in Children With Atopic Dermatitis: A Randomized Triple-Blind Clinical Trial," *J. Pediatr Pharmacol Ther*, vol. 28, No. 1, 2023.

Moaddel et al., "Identification of gingerenone A as a novel senolytic compound," PLOS ONE, vol. 17, No. 3, p. e0266135, Mar. 29, 2022.

Tenero, et al., "Anti-IL-5 in pediatric allergic diseases," *Abstract, Pediatr. Allergy Immul.*, Suppl 26:14-16, Nov. 31, 2020.

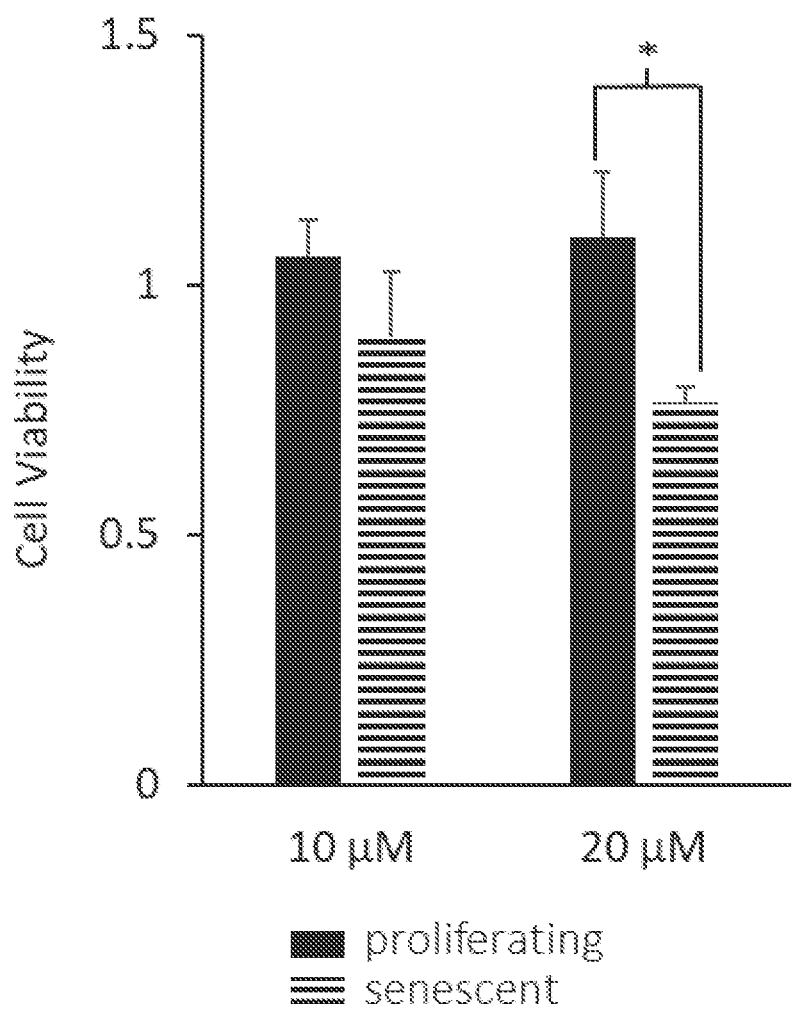

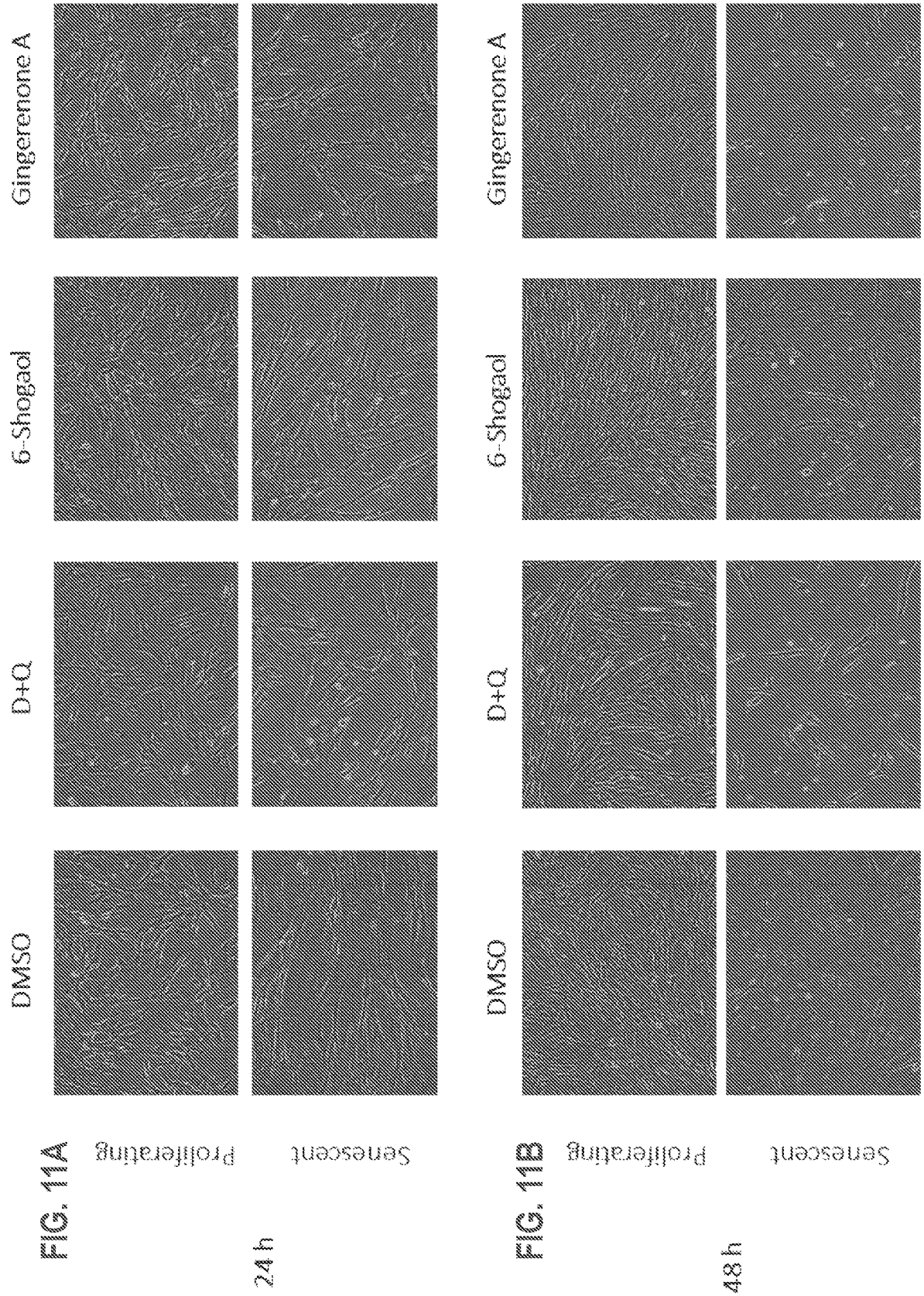

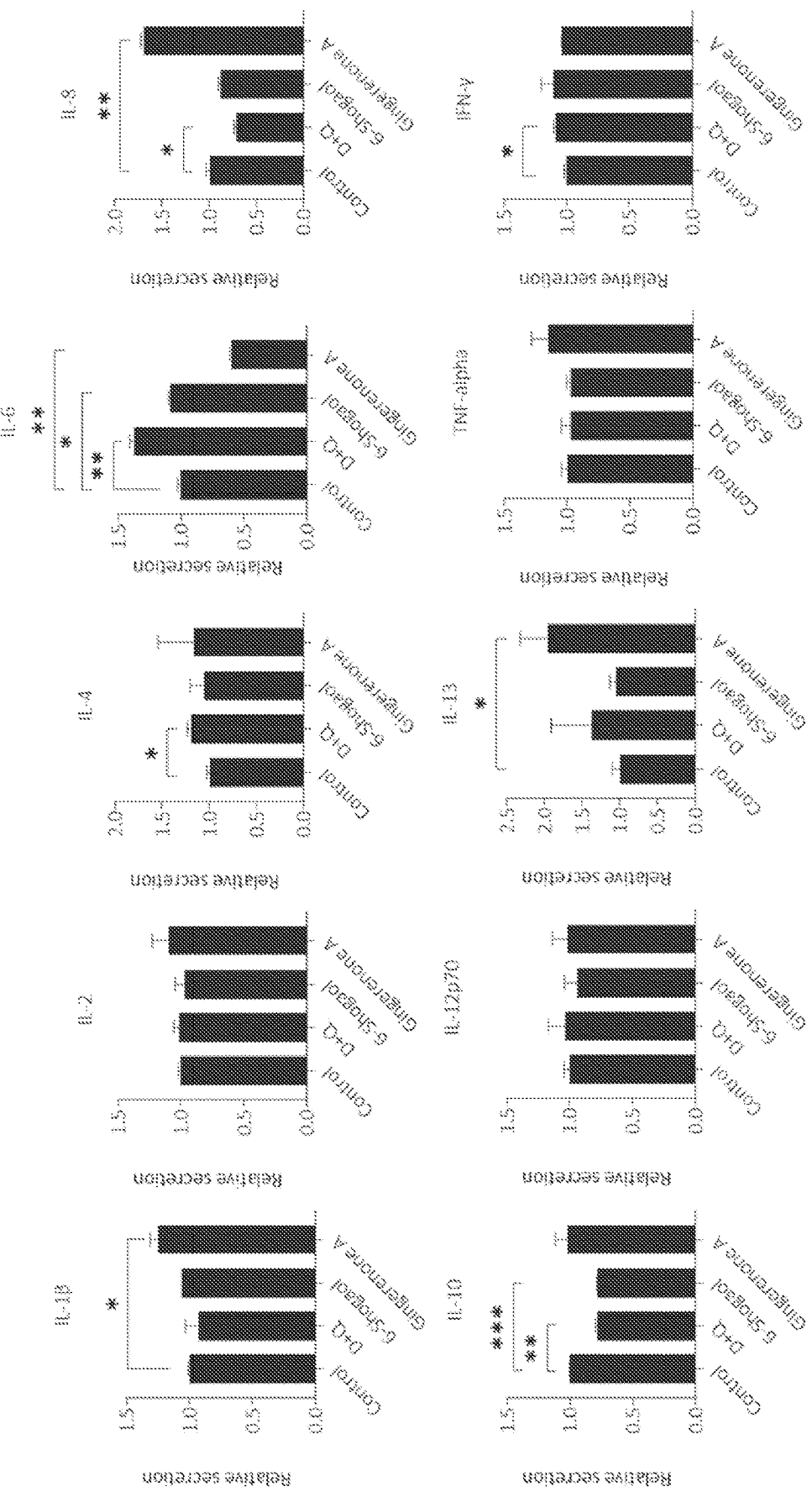

GINGERENONE A PRODRUGS AS SENSOTHERAPEUTICS AND METHODS OF USE

CROSS REFERENCE TO RELATED APPLICATIONS

This is the U.S. National Stage of International Application No. PCT/US2023/0010962, filed Jan. 17, 2023, which was published in English under PCT Article 21 (2), which in turn claims the benefit of U.S. Provisional Application No. 63/302,873, filed Jan. 25, 2022, each of which is incorporated herein in its entirety.

ACKNOWLEDGMENT OF GOVERNMENT SUPPORT

This invention was made with government support under project number Z01-AG-000295-18 awarded by the National Institutes of Health, National Institute on Aging. The government has certain rights in the invention.

FIELD

Gingerenone A prodrugs and methods of using the prodrugs are disclosed.

BACKGROUND

Cellular senescence accumulates with aging and is associated with several age-associated diseases and functional declines. Senescence is an enduring state of cell cycle arrest that occurs following exposure to different types of stresses. Senescence has anti-tumorigenic properties in young organisms by halting growth of damaged cells, but accumulation of senescent cells can be detrimental in older age as it promotes inflammation, tumorigenesis, and age-related pathologies.

Eliminating senescent cells with senolytic drugs has been shown to improve age phenotypes in mouse models and there is some initial evidence that it may improve the health of persons with chronic diseases. Senotherapeutics include senolytic drugs, which selectively eliminate senescent cells by apoptosis, and senomorphics, which suppress the pro-inflammatory senescence-associated secretory phenotype (SASP). Unfortunately, to-date very few senotherapeutic compounds have been identified.

Senescent cells display indefinite replication arrest, as first described by Hayflick (*Exp. Cell Res.* 1961, 25:585-621). These cells often show increased activity of the senescence-associated β-galactosidase (SA-βGal) at pH 6, and increased expression of TP53 (p53), CDKN1A (p21) and CDKN2A (p16) (Kuilman et al., *Genes & Development* 2010, 24(22):2463-2479). Despite their enduring growth arrest, they are metabolically active and display enhanced lysosomal activity. They also secrete a range of biologically active molecules, including pro-inflammatory cytokines, growth factors, and matrix metalloproteases, a trait known as the senescence-associated secretory phenotype (SASP) (Bhaumik et al., *Aging* 2009, 1(4):402-411). Senescence is a pleiotropic phenotype that can be beneficial in young age and detrimental in older age. For example, in young organisms, senescence was found to play a beneficial role in wound healing, tissue remodeling, embryonic development, and tumor suppression (Tominaga, *Pathobiol Aging Age Relat Dis.* 2015, 5:27743). However, the accumulation of senescent cells in aged tissues promotes premature aging, chronic inflammation, insulin resistance, liver fibrosis, atherosclerosis, neurodegenerative disorders, and cancer (McHugh et al., *Cell biol.* 2018, 271(1):65-77). In animal models, elimination of senescent cells by senolytic drugs or genetic approaches improves health span and slows down the development of aging phenotypes that are associated with functional impairment (Kirkland et al., *J Intern Med* 2020, 288(5):518-536). For example, the clearance of p16-positive senescent cells in the transgenic INK-ATTAC mouse improved age-associated pathologies such as atherosclerosis, neurodegeneration, sarcopenia, cataracts, cardiac hypertrophy, kidney disease, cancer, and osteoarthritis (Baker et al., *Nature* 2011, 479(7372):232-236; Childs et al., *Nature Reviews Drug Discovery* 2017, 16(10):718-735). Thus, the clearance of senescent cells provides a promising avenue to combat age-related accumulation of pathological condition and functional impairments by eliminating senescence-associated traits (Tchkonia et al., *J Clin Invest.* 2013, 123(3):966-972).

SUMMARY

Gingerenone A prodrugs and methods of using the prodrugs are disclosed. In some embodiments, the gingerenone A prodrug is a compound having a structure according to Formula I, or a stereoisomer, tautomer, or a pharmaceutically acceptable salt thereof:

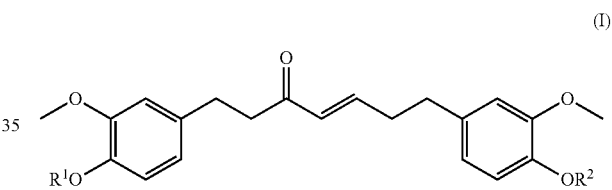

(I)

wherein one of $R^1$ and $R^2$ is —C(O)—R or H, and the other of $R^1$ and $R^2$ is —C(O)—R. Each R independently is $R^A$ or

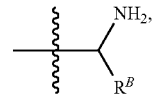

wherein $R^A$ is $C_{18}$-$C_{22}$ alkenyl and $R^B$ is an amino acid side chain.

In some implementations, $R^1$ and $R^2$ are —C(O)—$R^A$ where each $R^A$ independently is $C_{18}$-$C_{22}$ alkenyl. The alkenyl group may comprise two or more double bonds. In some embodiments, $R^1$ and $R^2$ independently are —C(O)—$(CH_2)_3$—(CH=CH—$CH_2)_5$—$CH_3$ or —C(O)—$(CH_2)_2$—(CH=CH—$CH_2)_6$—$CH_3$. In one implementation, $R^1$ and $R^2$ are the same. In another implementation, $R^1$ and $R^2$ are different.

In some embodiments, one of $R^1$ and $R^2$ is —C(O)—$R^A$ and the other of $R^1$ and $R^2$ is

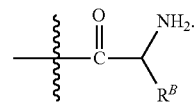

In certain implementations, one of $R^1$ and $R^2$ is

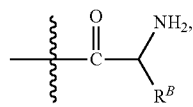

and the other of $R^1$ and $R^2$ is —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$.

A pharmaceutical composition includes a gingerenone A prodrug compound as disclosed herein and a pharmaceutically acceptable carrier.

In some embodiments, a method of inhibiting senescence includes contacting a senescent cell with an effective amount of a gingerenone A prodrug compound or a pharmaceutical composition comprising the compound. Inhibiting senescence may include killing the senescent cell, activating caspase-3 in the senescent cell, or a combination thereof. In some implementations, contacting is performed in vivo and the compound subsequently is cleaved in vivo to provide gingerenone A, $R^1$OH, and $R^2$OH.

In some embodiments, a method includes inhibiting or eliminating senescence, neuroinflammation, pain, or any combination thereof in a subject, the method comprising administering to the subject a therapeutically effective amount of a gingerenone A prodrug compound or a pharmaceutical composition comprising the compound. In certain embodiments, administering to the subject the therapeutically effective amount of the compound selectively kills senescent cells in the subject, activates caspase-3 in senescent cells in the subject, reduces secretion of interleukin-6 (IL-6) in the subject, reduces secretion of chemokine (C—C motif) ligand 2 (CCL2) in the subject, reduces secretion of interferon gamma-induced protein 10 (IP-10) in the subject, increases a level of interleukin-10 (IL-10) in the subject, increases a level of interleukin-13 (IL-13) in the subject, increases circulating levels of eicosapentaenoic acid in the subject, increases circulating levels of docosahexaenoic acid in the subject, increases circulating levels of 17-hydroxydocosahexanoic acid in the subject, reduces neuroinflammation in the subject, reduces frequency of physical pain in the subject, reduces intensity of physical pain in the subject, or any combination thereof.

In one implementation, the subject has a senescence-associated disease or disorder. In an independent implementation, the subject has an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, pain, or any combination thereof. In another independent implementation, the subject has atherosclerosis, heart failure, hypertension, cerebral infarction, cerebral hemorrhage, osteoporosis, renal disease, renal failure, frailty, cognitive impairment, Parkinson's disease, Alzheimer's disease, Huntington's disease, motor neuron dysfunction, hearing loss, cataract, glaucoma, macular degeneration, presbyopia, lung fibrosis, liver fibrosis, pancreatic fibrosis, oral submucosa fibrosis, chronic obstructive pulmonary disease, asthma, sarcopenia, muscle fatigue, eczema, psoriasis, hyperpigmentation, dysesthesia, eosinophilic dermatosis, reactive neutrophilic dermatosis, pemphigus, pemphigoid, immunobullous dermatosis, cutaneous lupus, a skin wound healing disorder, type 2 diabetes, cardiomegaly, liver cirrhosis, osteoarthritis, dyslipidemia, emaciation, cancer, a chemotherapeutic side effect, a radiotherapy side effect, neuroinflammation, pain, or any combination thereof.

In any of the foregoing or following embodiments, the compound or pharmaceutical composition may be administered via an oral, parenteral, intramuscular, subcutaneous, topical, sublingual, intraocular, intranasal, inhalation, intrarectal, or intra-aural route. In any of the foregoing or following embodiments, the compound, following administration, may be cleaved in vivo to provide gingerenone A, $R^1$OH, and $R^2$OH.

The foregoing and other objects, features, and advantages of the invention will become more apparent from the following detailed description, which proceeds with reference to the accompanying figures.

BRIEF DESCRIPTION OF THE DRAWINGS

FIG. 8A shows effects after IR senescence triggered by exposure to 10 Gy followed by culture for an additional 10 days. FIG. 8B shows impact on cell survival as determined by an MTT cell viability assay.

FIGS. 10A-10C show senolytic activity of gingerenone A. FIG. 10A shows the senolytic activity of major ginger extract components. FIG. 10B is a graph showing the dose response effect of gingerenone A. FIG. 10C is a bar graph demonstrating that 20 µM gingerenone A significantly decreased senescent cell viability relative to proliferating cells.

FIGS. 11A-11C show the senolytic effects in senescent cells treated with DMSO (vehicle), dasatinib and quercetin (D+Q), gingerenone A, or 6-shogaol, and incubated for 24 h (FIG. 11A) or 48 h (FIG. 11B), whereupon cell viability was assayed by MTT analysis; the micrographs are representative of three biological replicates. The graph in FIG. 11C shows the means and standard error from three biological replicates.

FIG. 12A is a bar graph showing effects on CCL-2 (MCP-1), IL-6, and IL-10. FIG. 12B is a Western blot of the proteins after treating proliferating and senescent WI-38 fibroblasts for 48 h with gingerenone A, 6-shogaol and D+Q.

FIGS. 13A and 13B are bar graphs showing cytokine (FIG. 13A) and chemokine (FIG. 13B) levels after treating proliferating and senescent WI-38 fibroblasts for 24 h with gingerenone A, 6-shogaol and D+Q.

DETAILED DESCRIPTION

Figure 1:
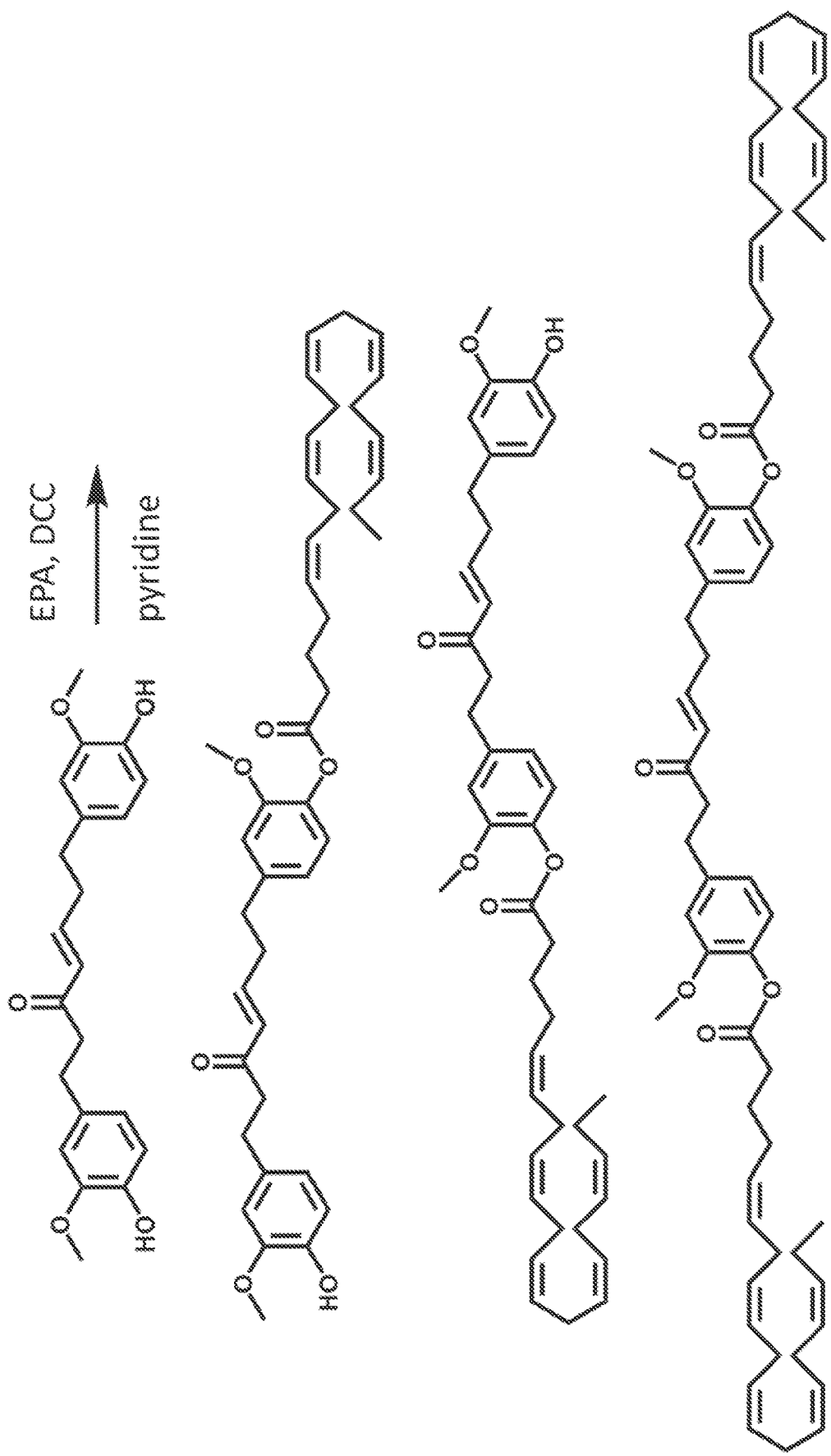
FIG. 1 is an exemplary scheme for synthesizing a gingerenone A prodrug comprising two eicosapentaenoic acid (EPA) ester groups.

This disclosure concerns embodiments of gingerenone A prodrugs, pharmaceutical compositions comprising the prodrugs, and methods of using the prodrugs. The prodrugs include one or two alkenyl ester groups that are cleaved in vivo to provide gingerenone A and alkenyl compounds. Both the gingerenone A and alkenyl compounds may have therapeutic benefits. Advantageously, some embodiments of the prodrugs exhibit increased bioavailability compared to gingerenone A, increased stability (e.g., shelf-life stability) and/or half-life compared to the alkenyl compounds, and/or exhibit synergistic benefits compared either the gingerenone A or alkenyl compound(s) alone. In some embodiments, therapeutically effective amounts of the prodrugs inhibit or eliminate senescence, neuroinflammation, pain, or any combination thereof, when administered to a subject.

I. DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0). The presently disclosed compounds also include all isotopes of atoms present in the compounds, which can include, but are not limited to, deuterium, tritium, $^{14}C$, etc. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Alkyl: A hydrocarbon group having a carbon chain containing or more double bonds.

Amino Acid: An organic acid containing both a basic amino group (—NH$_2$) and an acidic carboxyl group (—COOH). The amino acids that are protein constituents are α-amino acids, i.e., the —NH$_2$ group is attached to the carbon atom next to the —COOH group. A side chain also is attached to the carbon atom next to the —COOH group. An essential amino acid is an amino acid that cannot be made by the human body and is obtained from food.

Ester: A compound having a general formula:

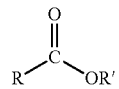

where R and R' denote virtually any group, including aliphatic, substituted aliphatic, aryl, arylalkyl, heteroaryl, etc.

Isomer: One of two or more molecules having the same number and kind of atoms, but differing in the arrangement or configuration of the atoms. Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. The E and Z isomers of 2-butene are shown below:

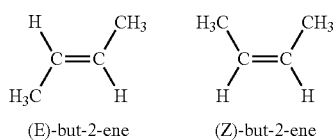

(E)-but-2-ene    (Z)-but-2-ene

Pharmaceutically acceptable carriers: The pharmaceutically acceptable carriers provided herein are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. For topical formulations, conventional carriers can include, for example, finely divided solids (e.g., talc, clay, microcrystalline cellulose, silica, alumina), liquid carriers (e.g., water, dimethyl sulfoxide, alcohols, glycols, and the like), and/or thickeners (synthetic polymers, fatty acids, fatty alcohols, celluloses, etc.). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. The pharmaceutical carriers also may, in some implementations, include liposomal carriers.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.) Senescence: Biological aging, gradual deterioration of functional characteristics in living organisms. Senescent means to be characterized by senescence, to be deteriorating.

Senolytic: As used herein, the term "senolytic" refers to a small molecule capable of selectively inducing death of senescent cells.

Senomorphic: As used herein, the term "senomorphic" refers to a small molecule capable of suppressing senescent phenotypes without killing the cells.

Senotherapeutic: A general term encompassing both senolytic and senomorphic compounds.

Subject: An animal (human or non-human) subjected to a treatment, observation or experiment. Includes both human and veterinary subjects, including human and non-human mammals, such as rats, mice, cats, dogs, pigs, horses, cows, and non-human primates.

Tautomers: Constitutional isomers of organic compounds that differ only in the position of the protons and electrons, and are interconvertible by migration of a hydrogen atom. Tautomers ordinarily exist together in equilibrium.

Therapeutically effective amount or dose: An amount sufficient to provide a beneficial, or therapeutic, effect to a subject or a given percentage of subjects.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. GINGERENONE A PRODRUGS

Gingerenone A is a compound found in extract from *Zingiber officinale* Rosc. (ginger):

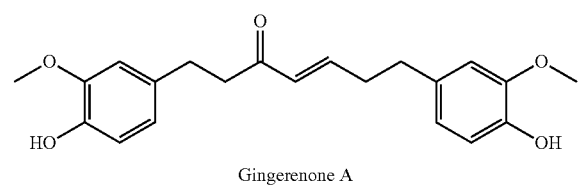

Gingerenone A

Gingerenone A has been found to reduce senescent cell viability as indicated by direct cell counting, enhance cleaved caspase-3, and decrease levels of the anti-apoptotic protein Bcl-XL. Further, gingerenone A decreases secretion of the SASP factor interleukin-6 (IL-6), a pro-inflammatory cytokine, decreases secretion of chemokine (C—C motif) ligand 2 (CCL2), reduces secretion of interferon gamma-induced protein 10 (IP-10), and increases levels of interleukin-13 (IL-13). Hence, gingerenone A is a promising natural senolytic compound. However, like many polyphenols, gingerenone A has limited bioavailability, such as limited oral bioavailability.

The inventors have solved the problem of limited bioavailability by synthesizing prodrugs of gingerenone A, wherein a cleavable ester group replaces one or both hydroxy groups on the gingerenone A molecule. Embodiments of the disclosed gingerenone A prodrugs have a structure according to Formula I, or a stereoisomer, tautomer, or a pharmaceutically acceptable salt thereof:

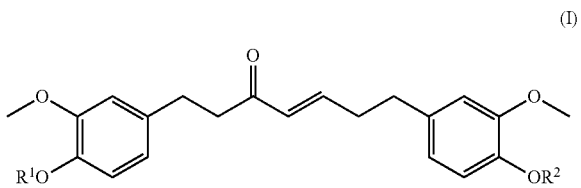
(I)

wherein at least one of $R^1$ and $R^2$ exhibits senolytic or senomorphic activity, or provides another therapeutic benefit (e.g., pain reduction). In some embodiments, one of $R^1$ and $R^2$ is —C(O)—R or H, and the other of $R^1$ and $R^2$ is —C(O)—R. Each R independently is $R^A$ or

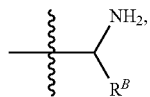

wherein $R^A$ is $C_{18}$-$C_{22}$ alkenyl and $R^B$ is an amino acid side chain. In some embodiments, $R^1$ and $R^2$ are —C(O)—$R^A$. In one implementation, $R^1$ and $R^2$ are the same. In an independent implementation, $R^1$ and $R^2$ are different. In some embodiments, one of $R^1$ and $R^2$ is —C(O)—$R^A$ and the other of $R^1$ and $R^2$ is

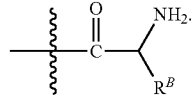

In one implementation, one of $R^1$ and $R^2$ is H and the other of $R^1$ and $R^2$ is —C(O)—$R^A$.

In any of the foregoing or following embodiments, each $R^A$ may independently comprise two or more double bonds. In some embodiments, each $R^A$ independently includes from two to ten double bonds, such as 2, 3, 4, 5, 6, 7, 8, 9, or 10 double bonds, such as 3-8, 4-7, or 5-6 double bonds.

In any of the foregoing or following embodiments, —C(O)$R^A$ may correspond to a long-chain polyunsaturated fatty acid, such as a long-chain omega-3 polyunsaturated fatty acid. For example, —C(O)$R^A$ may correspond to eicosapentaenoic acid (EPA) or docosahexaenoic acid (DHA). Advantageously, some long-chain polyunsaturated fatty acids may reduce inflammation, pain, hypertension, and/or risk of some chronic diseases (e.g., coronary heart disease). However, some long-chain polyunsaturated fatty acids, such as long-chain omega-3 polyunsaturated fatty acids, are susceptible to oxidation. Polyphenols, such as gingerenone A, are powerful antioxidants. Hence, the prodrug structure simultaneously may increase bioavailability of gingerenone A while preventing oxidation of the $C_{18}$-$C_{22}$ alkenyl groups, thereby increasing shelf-life stability of the prodrug relative to shelf-life stability of the corresponding long-chain polyunsaturated fatty acids.

In any of the foregoing or following embodiments, each $R^B$ may independently comprise an amino acid side chain. Amino acid side chains include —H, —$CH_3$, —CH($CH_3$)$_2$, —CH($CH_3$)$CH_2CH_3$, —$CH_2$CH($CH_3$)$_2$, —$(CH_2)_2SCH_3$, —$CH_2OH$, —CH(OH)$CH_3$, —$CH_2$C(O)$NH_2$, —$(CH_2)_2$C(O)$NH_2$, —$CH_2SH$, —$CH_2NH_2$, —$(CH_2)_3$N(H)C($=$NH)$NH_2$, —$(CH_2)_4NH_2$, —$CH_2COOH$, —$(CH_2)_2COOH$,

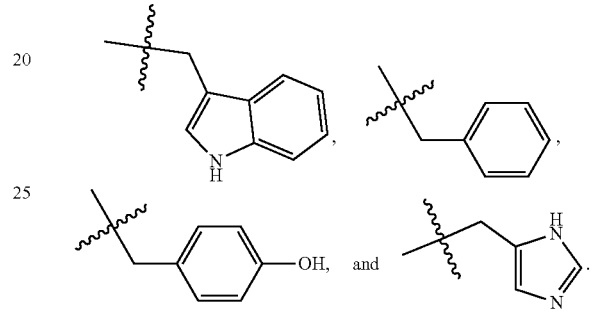

In certain implementations, $R^B$ is —$(CH_2)_4NH_2$.
Including a

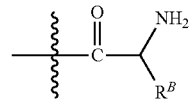

group at one of $R^1$ or $R^2$ may provide advantages. For example, the amino acid side chain facilitates formation of salts, which may improve solubility of the prodrug. Additionally, the

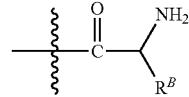

group may be cleaved from the prodrug to provide an amino acid. In some implementations, the cleaved amino acid is an essential amino acid. Essential amino acids for humans are histidine, isoleucine, leucine, lysine, methionine, phenylalanine, threonine, tryptophan, and valine. Thus, in some embodiments, $R^B$ is a side chain of an essential amino acid. In certain implementations, $R^B$ is a lysine, arginine, leucine, tyrosine, or tryptophan side chain. Lysine provides several health benefits including, but not limited to, collagen formation (Yamauchi et al., *Methods Mol biol.* 2019, 1934: 309-324) and improved wound healing (Spallota et al., *Communicative and Integrative Biol.* 2013, 6(5):e25466). Tryptophan and tyrosine may improve mood (Kikuchi et al., *J Diet Suppl.* 2021, 18(3):316-333; Jongkees et al., *J. Psychiatr Res.* 2015 November, 70:50-7). Leucine supplementation may counteract age-related loss of muscle mass (Rondanelli et al., *Front Nutr.* 2021 Jan. 26, 7:622391). Arginine may improve wound healing as well as several other age-related processes that decline with age (Tokarz et al., *Int. J of Molecular Sciences* 2021, 22(15):7958).

In some embodiments, $R^1$ and $R^2$ independently are —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$. In certain embodiments, one of $R^1$ and $R^2$ is

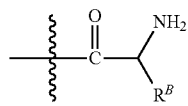

and the other of $R^1$ and $R^2$ is —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$. In some examples, $R^1$ is

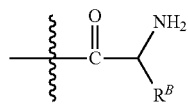

and $R^2$ is —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$. In some implementations, one of $R^1$ and $R^2$ is H and the other of $R^1$ and $R^2$ is —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$. In one embodiment, both $R^1$ and $R^2$ are —C(O)—(CH$_2$)$_3$—(CH=CH—CH$_2$)$_5$—CH$_3$. In an independent embodiment, both $R^1$ and $R^2$ are —C(O)—(CH$_2$)$_2$—(CH=CH—CH$_2$)$_6$—CH$_3$. In another independent embodiment, $R^1$ is

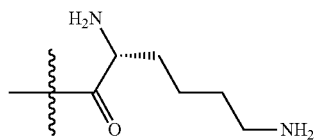

and $R^2$ is —C(O)—(CH$_2$)$_3$—(CH=CH—CH$_2$)$_6$—CH$_3$. In yet another independent embodiment, $R^1$ is

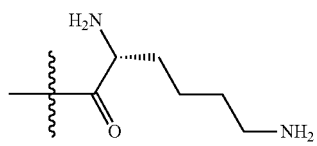 [SMILES: *C(=O)[C@H](N)CCCCN]

and $R^2$ is —C(O)—(CH$_2$)$_3$—(CH=CH—CH$_2$)$_6$—CH$_3$.

Exemplary compounds according to formula I include, but are not limited to:

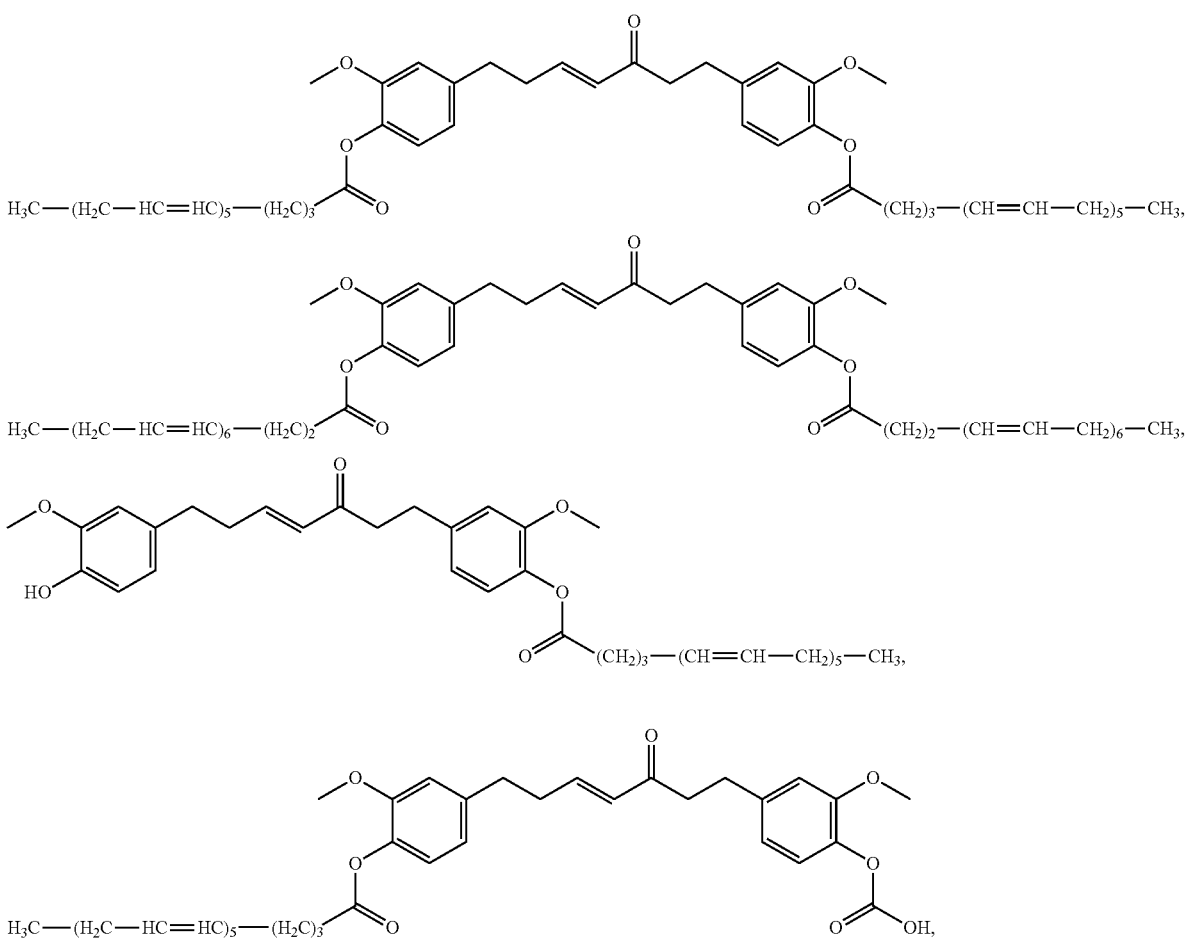

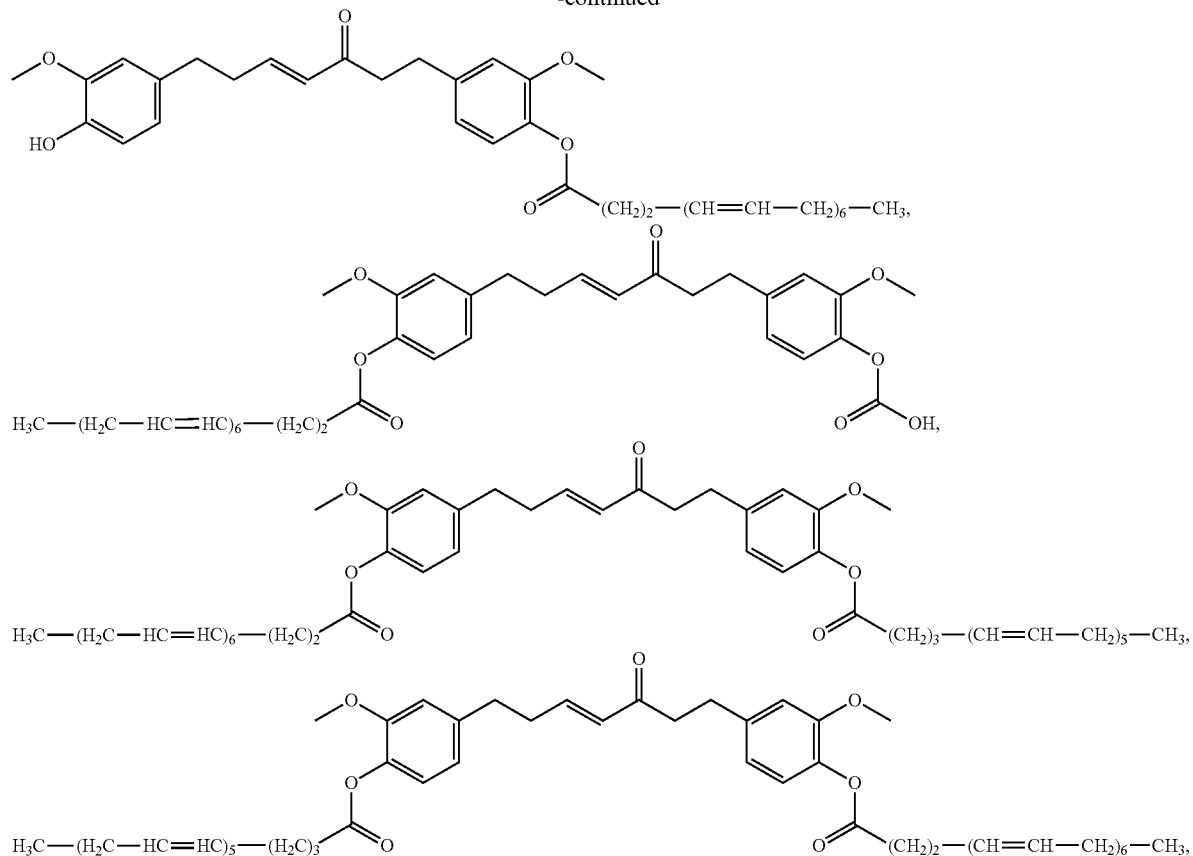
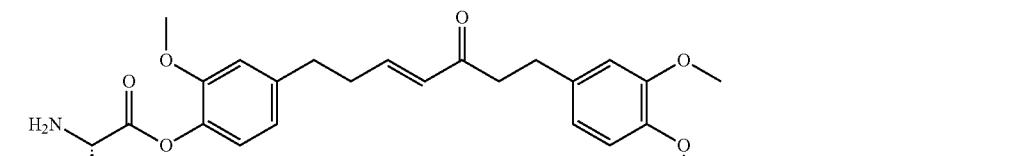
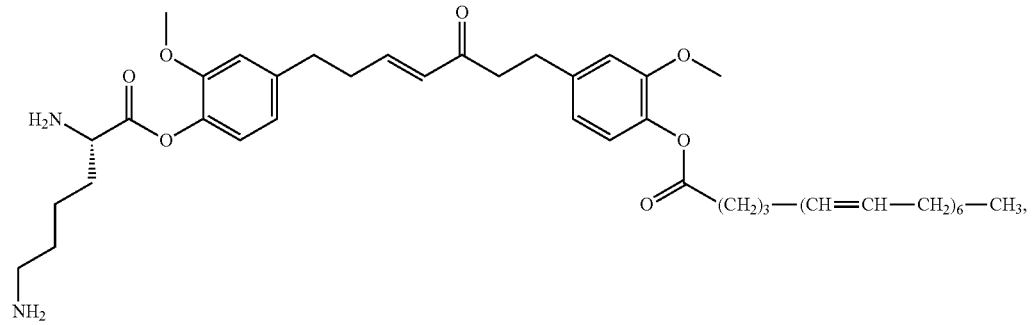
or a pharmaceutically acceptable salt thereof.

In particular examples, the compound is:

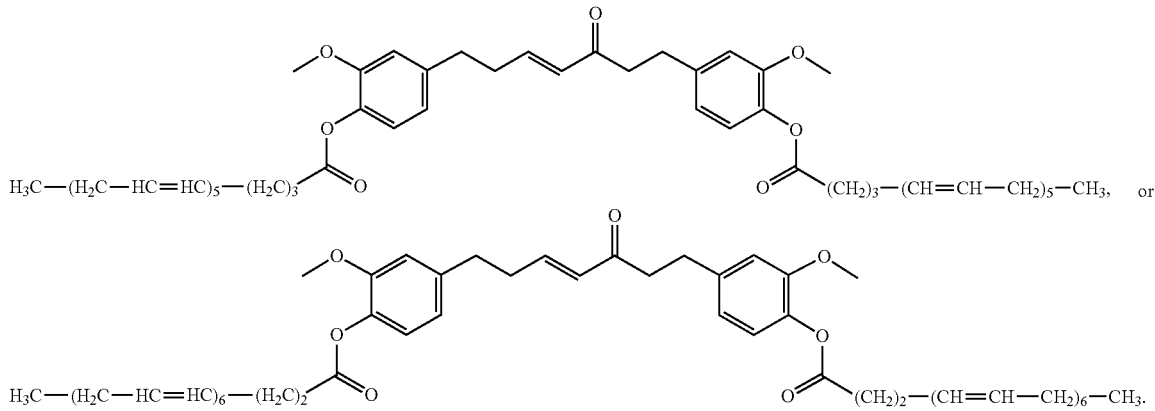

III. PHARMACEUTICAL FORMULATIONS

Another aspect of the disclosure includes pharmaceutical compositions prepared for administration to a subject and which include an effective amount of one or more of the prodrugs disclosed herein. The therapeutically effective amount of a disclosed prodrug will depend on the route of administration and the physical characteristics of the subject being treated. Specific factors that can be taken into account include disease severity and stage, weight, diet and concurrent medications. The relationship of these factors to determining a therapeutically effective amount of the disclosed prodrugs is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, PA, 19th Edition (1995), describes compositions and formulations suitable for pharmaceutical delivery of the prodrugs herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. For topical compositions (e.g., liquids, lotions, creams, ointments, pastes, and the like), conventional carriers include solid carriers (e.g., finely divided solids such as talc, clay, microcrystalline cellulose, silica, alumina, and the like), liquid carriers (e.g., water, dimethyl sulfoxide (DMSO), alcohols, glycols, or water-alcohol/glycol blends, optionally with the aid of non-toxic surfactants), and/or thickeners (e.g., synthetic polymers, fatty acids, fatty acid salts and esters, fatty alcohols, modified celluloses, or modified mineral materials). Adjuvants such as fragrances and additional antimicrobial agents can be added to optimize the properties for a given use. Liquid compositions can be applied from absorbent pads, used to impregnate bandages and other dressings, or sprayed onto the affected area using a pump-type or aerosol sprayer. Other topical formulations include spreadable pastes, gels, ointments, soaps, and the like, for application directly to the skin of the user.

In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the formulation may comprise a plurality of nanoparticles, the nanoparticles comprising the prodrug. In some implementations, the formulation may comprise a plurality of liposomes, the liposomes comprising (e.g., encapsulating) the prodrug.

The prodrug compounds described herein can be used to prepare therapeutic pharmaceutical compositions. The compounds may be added to the compositions in the form of a salt (e.g., when the compound is a mono-ester) or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and b-glycerophosphate. Suitable inorganic salts may also be formed, including hydrochloride, halide, sulfate, nitrate, bicarbonate, and carbonate salts.

Pharmaceutically acceptable salts may be obtained using procedures known to persons of ordinary skill in the art, for example by reacting a sufficiently basic compound, such as an amine, with a suitable acid to provide a physiologically acceptable ionic compound. Alkali metal (for example, sodium, potassium or lithium) or alkaline earth metal (for example, calcium) salts of carboxylic acids can also be prepared by analogous methods.

The prodrugs described herein can be formulated as pharmaceutical compositions and administered to a mammalian host, such as a human or veterinary patient, in a variety of forms. The pharmaceutical compositions can be administered to subjects by a variety of mucosal administration modes, including by oral, rectal, intranasal, intrapul monary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes.

To formulate the pharmaceutical compositions, the prodrug can be combined with various pharmaceutically acceptable additives, as well as a base or vehicle for dispersion of the prodrug. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The prodrug can be dispersed in a base or vehicle, which can include a hydrophilic compound having a capacity to disperse the prodrug, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The prodrug can be combined with the base or vehicle according to a variety of methods, and release of the prodrug can be by diffusion, disintegration of the vehicle, or associated formation of water channels. In some circumstances, the prodrug is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time. In some implementations, the prodrug is encapsulated within liposomes prepared from suitable lipids and dispersed in a biocompatible dispersing medium.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the prodrug can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the prodrug can be brought about by including in the composition an agent which delays absorption, for example, monostearate salts and gelatin.

In certain embodiments, the prodrug can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the prodrug and which is capable of incorporating the prodrug. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the prodrug in the required amount in an appropriate solvent with one or a combination of ingredients enumerated herein, as required, followed by filtered sterilization. Generally, dispersions are prepared by incorporating the prodrug into a sterile vehicle that contains a basic dispersion medium and the required other ingredients from those enumerated herein. In the case of sterile powders, methods of preparation include vacuum drying and freeze-drying which yields a powder of the prodrug plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the prodrugs described herein. In one example, this component is formulated in a pharmaceutical preparation for delivery to a subject. The prodrug is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

IV. METHODS OF USE

A method of inhibiting senescence may comprise contacting a senescent cell with an effective amount of a compound as disclosed herein or a pharmaceutical composition comprising the compound. In certain implementations, contacting is performed in vivo and the compound subsequently is cleaved in vivo to provide gingerenone A, $R^1OH$, and $R^2OH$, wherein $R^1$ and $R^2$ are defined as above. In some embodiments, inhibiting senescence comprises killing the senescent cell, activating caspase-3 in the senescent cell, or a combination thereof. Activating caspase-3 promotes apoptosis. In some embodiments, the compound is senomorphic and affects biomarkers associated with senescence. For example, the compound may decrease levels of interleukin-6 (IL-6), chemokine (C—C motif) ligand 2 (CCL2), and interferon gamma-induced protein 10 (IP-10). The compound also, or alternatively, may increase levels of interleukin-10 (IL-10) and/or interleukin-13 (IL-13).

Embodiments of a method of inhibiting or eliminating senescence, neuroinflammation, pain, or any combination thereof in a subject may comprise administering to the subject a therapeutically effective amount of a compound as disclosed herein or a pharmaceutical composition comprising the compound. In some embodiments, administering to the subject the therapeutically effective amount of the compound selectively kills senescent cells in the subject, activates caspase-3 in senescent cells in the subject, reduces secretion of interleukin-6 (IL-6) in the subject, reduces secretion of chemokine (C—C motif) ligand 2 (CCL2) in the subject, reduces secretion of interferon gamma-induced protein 10 (IP-10) in the subject, increases a level of interleukin-10 (IL-10) in the subject, increases a level of interleukin-13 (IL-13) in the subject, increases circulating levels of eicosapentaenoic acid in the subject, increases circulating levels of docosahexaenoic acid in the subject, increases circulating levels of 17-hydroxydocosahexanoic acid in the subject, reduces neuroinflammation in the subject, reduces frequency of physical pain in the subject, reduces intensity of physical pain in the subject, or any combination thereof.

In any of the foregoing or following embodiments, the subject may have a senescence-associated disease or disorder. Inhibiting senescence may improve, for example, cardiovascular disease (e.g., atherosclerosis), neurodegenerative diseases or disorders, sarcopenia, metabolic diseases or disorders, and/or other age-related diseases or disorders. In some embodiments, the subject has an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, pain, or any combination thereof. In certain implementations, the subject has atherosclerosis, heart failure, hypertension, cerebral infarction, cerebral hemorrhage, osteoporosis, renal disease, renal failure, frailty, cognitive impairment, Parkinson's disease, Alzheimer's disease, Huntington's disease, motor neuron dysfunction, hearing loss, cataract, glaucoma, macular degeneration, presbyopia, lung fibrosis, liver fibrosis, pancreatic fibrosis, oral submucosa fibrosis, chronic obstructive pulmonary disease, asthma, sarcopenia, muscle fatigue, eczema, psoriasis, hyperpigmentation, dysesthesia, eosinophilic dermatosis, reactive neutrophilic dermatosis, pemphigus, pemphigoid, immunobullous dermatosis, cutaneous lupus, a skin wound healing disorder, type 2 diabetes, cardiomegaly, liver cirrhosis, osteoarthritis, dyslipidemia, emaciation, cancer, a chemotherapeutic side effect, a radiotherapy side effect, neuroinflammation, pain, or any combination thereof.

In any of the foregoing or following embodiments, administering the therapeutically effective amount of the compound or pharmaceutical composition comprising the compound to a subject having a disease or disorder as disclosed herein may treat the disease or disorder by inhibiting or eliminating the disease or disorder. Inhibiting the disease or disorder may comprise reducing or eliminating one or more signs or symptoms of the disease or disorder. In certain implementations, the therapeutically effective amount of the compound or pharmaceutical composition comprising the compound may be administered prophylactically to the subject to prevent or minimize the risk of developing a disease or disorder as disclosed herein. In some embodiments, inhibiting or eliminating the disease or disorder, or preventing the disease or disorder, comprises selectively killing senescent cells in the subject, activating caspase-3 in senescent cells in the subject, reducing secretion of interleukin-6 (IL-6) in the subject, reducing secretion of chemokine (C—C motif) ligand 2 (CCL2) in the subject, reducing secretion of interferon gamma-induced protein 10 (IP-10) in the subject, increasing a level of interleukin-10 (IL-10) in the subject, increasing a level of interleukin-13 (IL-13) in the subject, increasing circulating levels of eicosapentaenoic acid in the subject, increasing circulating levels of docosahexaenoic acid in the subject, increasing circulating levels of 17-hydroxydocosahexanoic acid in the subject, reducing neuroinflammation in the subject, reducing frequency of physical pain in the subject, reducing intensity of physical pain in the subject, or any combination thereof.

In certain implementations $R^1$ and/or $R^2$ correspond to long-chain polyunsaturated fatty acids, such as EPA and DHA. Two randomized clinical trials have shown that increasing circulating EPA and DHA reduces the frequency and intensity of physical pain by 30-40% (see, e.g., Ramsden et al., *BMJ* 2021, 374:n1448; Ramsden et al., *Pain* 2013, 154(11):2441-2451; Ramsden et al., *Pain* 2015, 16(8):707-716; Ramsden et al., *Pain* 2015, 156(4):587-596; Ramsden et al., *Prostaglandins Leukot Essent Fatty Acids* 2012, 87(4-5)135-141). Additionally, several studies in neuropathic pain models have shown that EPA and DHA have acute antinociceptive effects (Redivo et al., *Behav Brain Res.* 2019, 372:111992; Unda et al., *J Pharm Pharmacol.* 2020, 72(3):437-447), with EPA and DHA demonstrating anti-neuroinflammatory activity and regenerative properties after peripheral nerve injury (Unda et al., *J Pharm Pharmacol.* 2020, 72(3):437-447). Polyphenols are powerful antioxidants, and pre-clinical experimental evidence has demonstrated the antinociceptive effects of polyphenolic compounds in animal models of neuropathic pain (see, e.g., Boadas-Vaello et al., *Curr Drug Targets* 2017, 18(2):160-173). Thus, embodiments of the disclosed prodrugs when cleaved in vivo may exhibit senolytic/senomorphic effects in combination with pain relief (including neuropathic pain), reduced neuroinflammation, and/or regenerative properties after peripheral nerve injury. In some embodiments, the gingerenone A and long-chain polyunsaturated fatty acids act together synergistically to inhibit or eliminate senescence and/or inhibit or eliminate pain.

In some implementations, one of $R^1$ and $R^2$ corresponds to an amino acid when cleaved. In certain examples, the amino acid is an essential amino acid. The presence of an amino acid side chain may facilitate forming a soluble salt of the prodrug, thereby improving drug solubility. When cleaved, the amino acid may increase levels of the amino acid in the subject and/or provide additional health benefits, such as collagen formation, improved wound healing, improved mood, reduced age-related loss of muscle mass, and/or a reduction in other age-related processes that decline with age. In some embodiments, the gingerenone A, long-chain polyunsaturated fatty acid, and amino acid act together synergistically to inhibit or eliminate senescence, inhibit or eliminate pain, and/or provide other health benefits attributable to the amino acid as described herein.

The effective amount of the prodrug will depend upon the severity of the indication (e.g., senescence, neuroinflammation, pain, amino acid deficiency, or any combination thereof) and the general state of the subject's health. An effective amount is that which provides either subjective relief of one or more signs or symptoms or an objectively identifiable improvement as noted by the clinician or other qualified observer. In one embodiment, an effective amount is the amount necessary to selectively kill senescent cells in the subject, activate caspase-3 in senescent cells in the subject, reduce secretion of interleukin-6 (IL-6) in the subject, reduce secretion of chemokine (C—C motif) ligand 2 (CCL2) in the subject, reduce secretion of interferon gamma-induced protein 10 (IP-10) in the subject, increase a level of interleukin-10 (IL-10) in the subject, increase a level of interleukin-13 (IL-13) in the subject, increase circulating levels of eicosapentaenoic acid in the subject, increase circulating levels of docosahexaenoic acid in the subject, increase circulating levels of 17-hydroxydocosahexanoic acid in the subject, increase circulating levels of an amino acid in the subject, reduce neuroinflammation in the subject, reduce frequency of physical pain in the subject, reduce intensity of physical pain in the subject, or any combination thereof. In another embodiment, an effect amount is the amount necessary to reduce at least one sign or symptom of an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, pain, or any combination thereof. In another embodiment, an effect amount is the amount necessary to reduce at least one sign or symptom of atherosclerosis, heart failure, hypertension, cerebral infarction, cerebral hemorrhage, osteoporosis, renal disease, renal failure, frailty, cognitive impairment, Parkinson's disease, Alzheimer's disease, Huntington's disease, motor neuron dysfunction, hearing loss, cataract, glaucoma, macular degeneration, presbyopia, lung fibrosis, liver fibrosis, pancreatic fibrosis, oral submucosa fibrosis, chronic obstructive pulmonary disease, asthma, sarcopenia, muscle fatigue, eczema, psoriasis, hyperpigmentation, dysesthesia, eosinophilic dermatosis, reactive neutrophilic dermatosis, pemphigus, pemphigoid, immunobullous dermatosis, cutaneous lupus, a skin wound healing disorder, type 2 diabetes, cardiomegaly, liver cirrhosis, osteoarthritis, dyslipidemia, emaciation, cancer, a chemotherapeutic side effect, a radiotherapy side effect, neuroinflammation, pain, or any combination thereof. The effective amount of the agents administered can vary depending upon the desired effects and the subject to be treated.

The actual dosage of the prodrug will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the prodrug for eliciting the desired response in the subject. Dosage regimens can be adjusted to provide an optimum prophylactic or therapeutic response. An effective amount is also one in which any toxic or detrimental side effects of the prodrug is outweighed in clinical terms by therapeutically beneficial effects. A non-limiting range for an effective amount of a prodrug within the methods and formulations of the disclosure is 0.01 mg/kg body weight to 50 mg/kg body weight, such as 0.05 mg/kg to 50 mg/kg body weight, 0.2 mg/kg to 50 mg/kg body weight, 1 mg/kg to 50 mg/kg, 5 mg/kg to 50 mg/kg, 10 mg/kg to 50 mg/kg, 10 mg/kg to 40 mg/kg, 10 mg/kg to 35 mg/kg, 10 mg/kg to 30 mg/kg, or 15 mg/kg to 25 mg/kg. In an independent embodiment, the effective amount may an amount effective to provide an in vivo prodrug or gingerenone A concentration of 0.1-100 µM within the subject's blood stream, such as a concentration of 2.5-100 µM, 2.5-75 µM, 5-75 µM, 5-50 µM, 10-50 µM, 10-40 µM, 10-25 µM, or 15-25 µM.

Dosage can be varied by the attending clinician as previously described, such as based on a determined level of the one or more indicators associated with AD. Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

For prophylactic and therapeutic purposes, the prodrug can be administered to the subject by the oral route or in a single bolus delivery, via continuous delivery (for example, continuous intravenous delivery) over an extended time period, or in a repeated administration protocol (for example, by an hourly, daily or weekly, repeated administration protocol). The effective dosage of the prodrug can be provided as repeated doses within a prolonged prophylaxis or treatment regimen that will yield clinically significant results to alleviate one or more symptoms associated with senescence, neuroinflammation, pain, or any combination thereof and/or at least partially normalize a level of one or more indicators associated with senescence, neuroinflammation, pain, or any combination thereof. Determination of effective dosages in this context is typically based on animal model studies followed up by human clinical trials and is guided by administration protocols that significantly reduce the occurrence or severity of symptoms or at least partially normalize the level of the one or more indicators in the subject. The indicators may include, but are not limited to, caspase-3, cytokines, chemokines, and combinations thereof. Exemplary cytokines and chemokines include interleukin (IL)-1β (IL-1β), IL-2, IL-4, IL-6, IL-8, IL-10, IL-2p70, IL-30, tumor necrosis factor alpha (TNF-α), interferon gamma (IFN-γ), interferon gamma-induced protein 10 (IP-10), monocyte chemoattractant protein-1 (MCP-1)/chemokine (C—C motif) ligand 2 (CCL2), eotaxin, eotaxin-3, MCP-4, thymus- and activation-regulated chemokine (TARC), macrophage inflammatory protein 1α (MIP-1α), MIP-1β, or any combination thereof. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer an effective amount of the prodrug.

Treatment can involve daily or multi-daily doses of prodrug(s) over a period of a few days to months, or even years. Thus, the dosage regimen will also, at least in part, be determined based on the particular needs of the subject to be treated and will be dependent upon the judgment of the administering practitioner. In particular examples, the subject is administered a therapeutic composition that includes one or more of the disclosed prodrugs on a multiple daily dosing schedule, such as at least two consecutive days, 10 consecutive days, and so forth, for example for a period of weeks, months, or years. In one example, the subject is administered the composition for a period of at least 30 days, such as at least 2 months, at least 4 months, at least 6 months, at least 12 months, at least 24 months, at least 36 months, at least 5 years, at least 10 years, or indefinitely for the remainder of the subject's life.

In some embodiments, the subject may further be administered additional therapeutic agents. For example, the subject may be administered one or more additional therapeutic agents used for treating an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, pain, or any combination thereof, or for treating a sign or symptom of an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, or any combination thereof. Preparation and dosing schedules for the additional agent may be used according to manufacturer's instructions or as determined empirically by the skilled practitioner. The combination therapy may provide synergy and prove synergistic, that is, the effect achieved when the prodrug and therapeutic agent used together is greater than the sum of the effects that results from using the prodrug and therapeutic agent separately. A synergistic effect may be attained when the prodrug and additional therapeutic agent are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the prodrug and therapeutic agent are administered or delivered sequentially, for example by different injections in separate syringes. In general, during alternation, an effective dosage of the prodrug and of the therapeutic agent is administered sequentially, i.e. serially, whereas in combination therapy, effective dosages of the prodrug and therapeutic agent are administered together.

V. REPRESENTATIVE EMBODIMENTS

Certain representative embodiments are exemplified in the following numbered clauses.

1. A compound having a structure according to Formula I, or a stereoisomer, tautomer, or a pharmaceutically acceptable salt thereof:

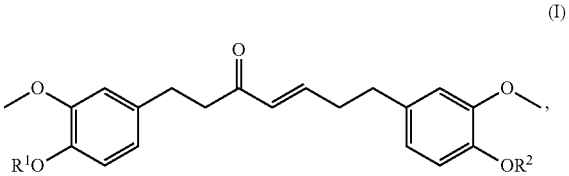

(I)

wherein one of $R^1$ and $R^2$ is H or —C(O)—R and the other of $R^1$ and $R^2$ is —C(O)—R, where each R independently is $C_{18}$-$C_{22}$ alkenyl.

2. The compound of clause 1, wherein $R^1$ and $R^2$ are —C(O)—R where each R independently is $C_{18}$-$C_{22}$ alkenyl.
3. The compound of clause 1 or clause 2, wherein R comprises two or more double bonds.
4. The compound of any one of clauses 1-3, wherein $R^1$ and $R^2$ are the same.
5. The compound of any one of clauses 1-3, wherein $R^1$ and $R^2$ are different.
6. The compound of any one of clauses 1-5, wherein $R^1$ and $R^2$ independently are —C(O)—$(CH_2)_3$—$(CH=CH-CH_2)_5$—$CH_3$ or —C(O)—$(CH_2)_2$—$(CH=CH-CH_2)_6$—$CH_3$.
7. The compound of clause 1, wherein the compound is:

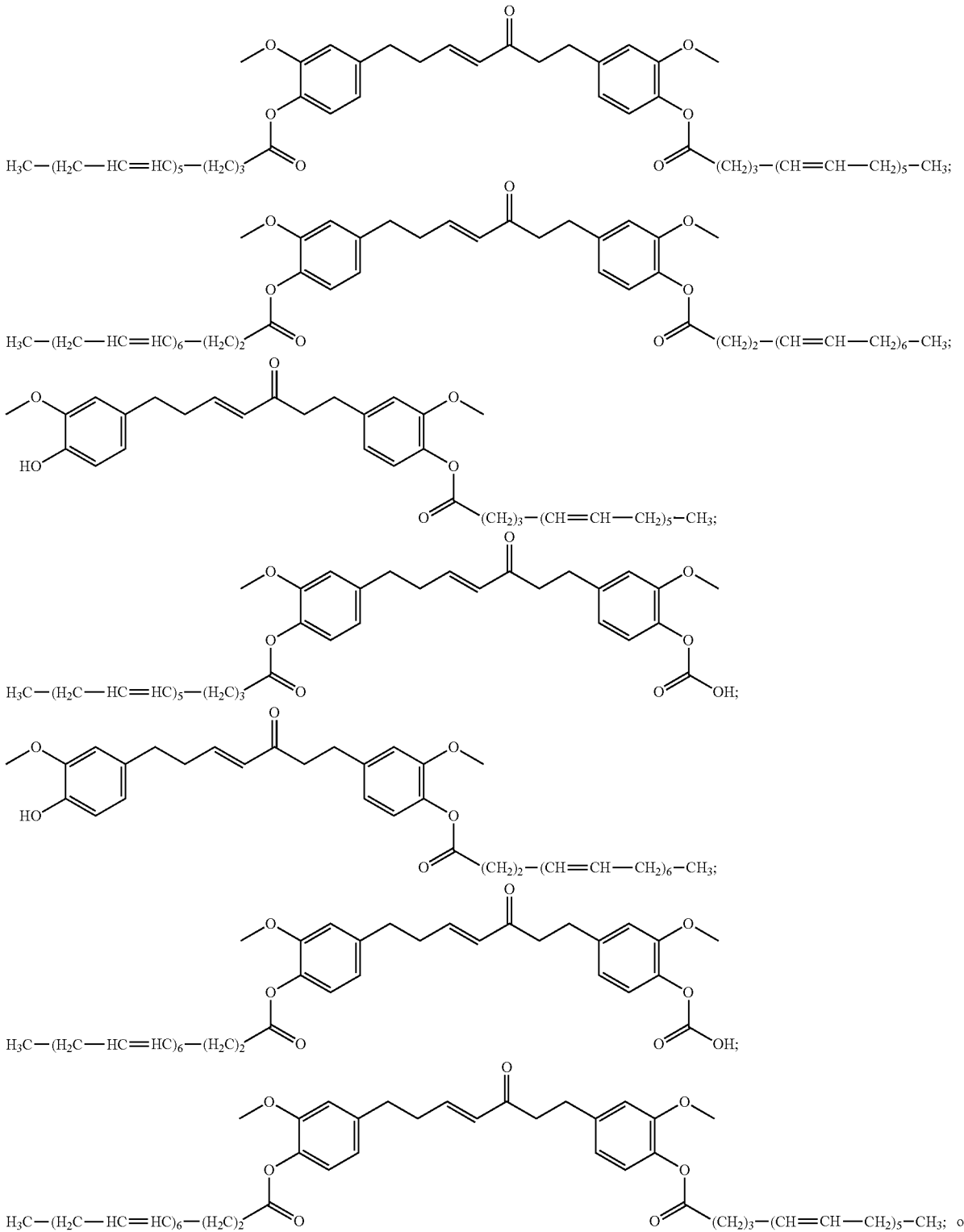

-continued

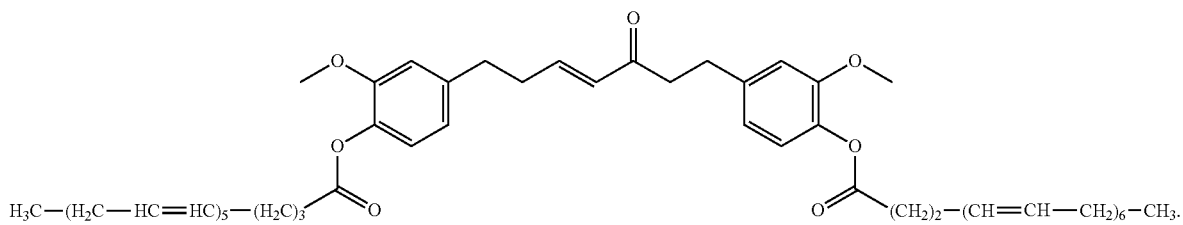

8. A pharmaceutical composition comprising: a compound according to any one of clauses 1-7; and a pharmaceutically acceptable carrier.

9. A method of inhibiting senescence, comprising contacting a senescent cell with an effective amount of a compound according to any one of clauses 1-7 or a pharmaceutical composition according to clause 8.

10. The method of clause 9, wherein inhibiting senescence comprises killing the senescent cell, activating caspase-3 in the senescent cell, or a combination thereof.

11. The method of clause 9 or clause 10, wherein contacting is performed in vivo and the compound subsequently is cleaved in vivo to provide gingerenone A, $R^1OH$, and $R^2OH$.

12. A method of inhibiting or eliminating senescence, neuroinflammation, pain, or any combination thereof in a subject, the method comprising administering to the subject a therapeutically effective amount of a compound according to any one of clauses 1-7 or a pharmaceutical composition according to clause 8.

13. The method of clause 12, wherein administering to the subject the therapeutically effective amount of the compound selectively kills senescent cells in the subject, activates caspase-3 in senescent cells in the subject, reduces secretion of interleukin-6 (IL-6) in the subject, reduces secretion of chemokine (C—C motif) ligand 2 (CCL2) in the subject, reduces secretion of interferon gamma-induced protein 10 (IP-10) in the subject, increases a level of interleukin-10 (IL-10) in the subject, increases a level of interleukin-13 (IL-13) in the subject, increases circulating levels of eicosapentaenoic acid in the subject, increases circulating levels of docosahexaenoic acid in the subject, increases circulating levels of 17-hydroxydocosahexanoic acid in the subject, reduces neuroinflammation in the subject, reduces frequency of physical pain in the subject, reduces intensity of physical pain in the subject, or any combination thereof.

14. The method of clause 12 or clause 13, wherein the subject has a senescence-associated disease or disorder.

15. The method of clause 12 or clause 13, wherein the subject has an age-related disease or disorder, a neurological disease or disorder, an inflammatory disease or disorder, a proliferative disease or disorder, a metabolic disease or disorder, a pulmonary disease or disorder, a renal disease or disorder, a neurological disease or disorder, an eye disease or disorder, a dermatologic disease or disorder, pain, or any combination thereof.

16. The method of clause 12 or clause 13, wherein the subject has atherosclerosis, heart failure, hypertension, cerebral infarction, cerebral hemorrhage, osteoporosis, renal disease, renal failure, frailty, cognitive impairment, Parkinson's disease, Alzheimer's disease, Huntington's disease, motor neuron dysfunction, hearing loss, cataract, glaucoma, macular degeneration, presbyopia, lung fibrosis, liver fibrosis, pancreatic fibrosis, oral submucosa fibrosis, chronic obstructive pulmonary disease, asthma, sarcopenia, muscle fatigue, eczema, psoriasis, hyperpigmentation, dysesthesia, eosinophilic dermatosis, reactive neutrophilic dermatosis, pemphigus, pemphigoid, immunobullous dermatosis, cutaneous lupus, a skin wound healing disorder, type 2 diabetes, cardiomegaly, liver cirrhosis, osteoarthritis, dyslipidemia, emaciation, cancer, a chemotherapeutic side effect, a radiotherapy side effect, neuroinflammation, pain, or any combination thereof.

17. The method of any one of clauses 12-16, wherein the compound or pharmaceutical composition is administered via an oral, parenteral, intramuscular, subcutaneous, topical, sublingual, intraocular, intranasal, inhalation, intrarectal, or intra-aural route.

18. The method of any one of clauses 12-17, wherein the compound, following administration, is cleaved in vivo to provide gingerenone A, $R^1OH$, and $R^2OH$.

19. The method of any one of clauses 12-18, wherein: $R^1$ and $R^2$ independently are —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$; or one of $R^1$ and $R^2$ is C(O)—(CH$_2$)$_3$—(CH=CH—CH$_2$)$_5$—CH$_3$ or —C(O)—(CH$_2$)$_2$—(CH=CH—CH$_2$)$_6$—CH$_3$, and the other of $R^1$ and $R^2$ is H.

20. The method of any one of clauses 12-18, wherein the compound is

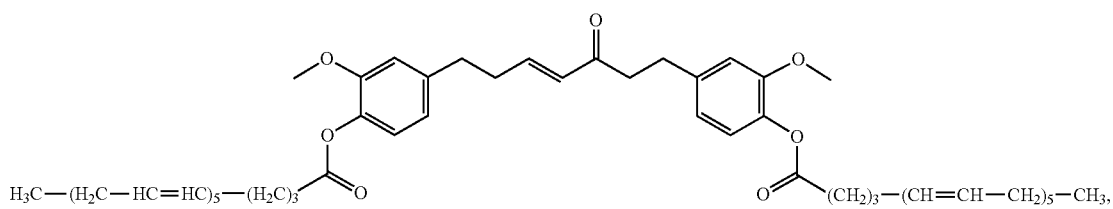

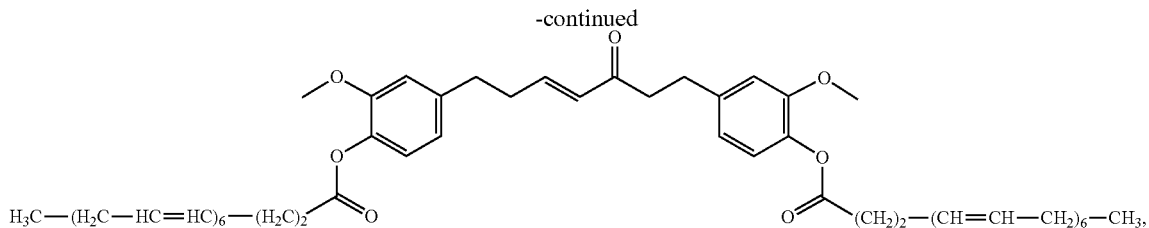

or a combination thereof.

VI. EXAMPLES

Materials:

Gingerenone A was purchased from Aobious (Gloucester, MA) and 6-shogaol, dasatinib and zingerone were purchased from Cayman Chemical (Ann Arbor, MI). 6-gingerol, 8-gingerol 10-gingerol, 8-shogaol and quercetin were purchased from Sigma-Aldrich (Milwaukee, WI). Cell counting was performed by using a TC20 Automated Cell Counter (Bio-Rad, Hercules, CA). Pictures were acquired by using a digital camera system (Nikon Digital Sight) for microscope (Nikon Eclipse S100) (Nikon Instruments, Melville, NY). *Harpagophytum procumbens* (Devil's Claw) (herb to menstruum ratio, 1:3), *Uncaria tomentosa* (Cat's Claw) (herb to menstruum ratio, 1:3), *Zingiber officinale* Rosc. (ginger) (herb to menstruum ratio, 1:3) and Canadian Golden Rod (herb to menstruum ratio, 1:3) were purchased from Galen's Way (Sebastopol, CA). The MTT assay was purchased from BioVision (Milpitas, CA). Senescence β-Galactosidase Staining Kit, ID #9860S was purchased from Cell Signaling Technology (Danvers, MA). Primary antibodies recognizing p21, p53, Beta-Actin (ACTB) were purchased from Santa Cruz Biotechnology (Dallas, Texas), primary antibodies recognizing caspase-3 were purchased from Abcam (Cambridge, MA) and Bcl-XL from Cell Signaling (Danvers, MA). IL-6 expression was measured by the Quantikine ELISA Kit purchased from R&D systems (Minneapolis, MN). Cytokines and chemokines were measured by multiplex assays including customized Luminex plates purchased from R &D (Minneapolis, MN) and V-Plex plus Proinflammatory panel 1 Human kit and the Chemokine Panel 1 Kit were purchased from Mesoscale Diagnostics (Rockville, MD).

Methods:

Cell culture and treatments: WI-38 human diploid fibroblasts (HDFs) were cultured in Dulbecco's modified Eagle's medium (DMEM) supplemented with 10% heat-inactivated fetal bovine serum (FBS), penicillin and streptomycin, and non-essential amino acids at 37° C. in a 5% $CO_2$ incubator. HDFs were rendered senescent by exposure to 10 Gy of ionizing radiation (IR) and then cultured for an additional ten days. Proliferating and senescent WI-38 cells were seeded in triplicate overnight at $2 \times 10^5$ cells/well (in 6 well plates) to achieve ~60% confluence by the next day. Cells were then treated with the extracts for times indicated.

In 24-well plates, cells were treated with multiple dilutions (1:200 and 1:500) of *Harpagophytum procumbens* (Devil's Claw) (herb to menstruum ratio, 1:3), *Uncaria tomentosa* (Cat's Claw) (herb to menstruum ratio, 1:3), *Zingiber officinale* Rosc. (ginger) (herb to menstruum ratio, 1:3) and Canadian Golden Rod (herb to menstruum ratio, 1:3) (Galen's Way, Sebastopol, CA). In 6-well plates, cells were treated for 24 or 48 h with the corresponding amount of DMSO (0.1%), D+Q (250 nM dasatinib and 10 µM quercetin, a known senolytic cocktail), gingerenone A (20 µM) and 6-shogaol (72.4 nM). Cell counting was performed by using a TC20 Automated Cell Counter (BioRad). Pictures were acquired by using a digital camera system (Nikon Digital Sight) for microscope (Nikon Eclipse TS100).

MTT cell viability: The MTT assay (BioVision Milpitas, CA) was carried out following the manufacturer's protocol. Briefly, the media was gently removed from each well and 50 µl of serum-free medium+50 µl of Solution A were added to each well. The plates were incubated at 37° C. for MTT reduction into formazan for 3 h. Next, 150 µl Solution B was added to each well and the plate was covered with foil and shaken at 600 rpm for 15 min. The absorbance was measured at 590 nm using Enspire, Perkin Elmer Multimode plate reader.

SA-βGal assay: Senescence-associated β-galactosidase (SA-βGal) activity in WI-38 cells was assessed by the Senescence β-Galactosidase Staining Kit following the manufacturer's protocol (Cell Signaling Technology). Briefly, the growth medium was aspirated from the 24-well plates, the wells were washed once with 0.5 ml of 1×PBS, 250 µl of Fixative solution (1×) was added to each well, and the plate was incubated at room temperature for 15 min. The solution was removed, the wells were washed twice with 0.5 ml of 1×PBS, and 250 µl of 1×SA-βGal detection solution was added. The plate was sealed with parafilm to prevent evaporation and was incubated overnight at 37° C. with no $CO_2$. The SA-βGal detection solution was removed, 250 µl of 1×PBS was added, and the plate was gently shaken for 1 h at room temperature. The PBS was removed, and 70% glycerol was added to each well for long term storage.

Protein analysis: Cells were lysed in RIPA lysis buffer (Pierce, ThermoFisher) containing protease and phosphatase inhibitors (Roche) and incubated on ice for 10 min. The lysates were then sonicated for 5 min and centrifuged for 10 min at 4° C. to remove the insoluble fraction. The remaining supernatant was the whole-cell lysate. Lysates were separated by SDS-polyacrylamide gel electrophoresis (SDS-PAGE) and transferred onto nitrocellulose membranes (Biorad). Incubations with primary antibodies recognizing p21, p53, Beta-Actin (ACTB) (Santa Cruz Biotechnology), as well as caspase-3 (Abcam) and Bcl-XL (Cell Signaling) were followed by incubations with the appropriate secondary antibodies conjugated with horseradish peroxidase (GE Healthcare). Signals were developed using Enhanced Chemiluminescence (ECL) and acquired by using the ChemiDoc MP Imaging System (BioRad).

Secreted protein analysis—ELISA, Luminex Multiplex and V-PLEX: Media was collected at the earliest timepoint (24 h after treatments) to avoid cell death that could interfere with the assay. The media was centrifuged at 1000×g for 5 min to remove debris. The secretion of IL-6 was measured by the Quantikine ELISA Kit (R&D systems) and the expression of pro-inflammatory cytokines and chemokines [IL-6, TNFα, CCL2 (MCP-1), IL-8, IFNβ] was also assessed by multiplex assays (customized Luminex plate, R&D) according to the manufacturer's instructions. The V-PLEX Plus Proinflammatory Panel 1 Human Kit and the Chemokine Panel 1 preparation and detection were carried out following the manufacturer's protocol (Mesoscale Diagnostics) using >80% confluency of proliferating or senescent cells on 24-well plates. Briefly, different concentrations of standards and samples were added to the plates, and they were incubated for 2 h on a microplate shaker. The plates were washed, and the corresponding detection antibody mixture was added to each well and incubated for 1 h with shaking. The plates were washed twice then Read buffer was added to each well. The plates were read on the MESO Quickplex SQ 120 (MSD, Rockville, MD) and protein concentrations were determined using MSD Discovery workbench 4.0.

Gingerenone A Quantification: The analysis of Gingerenone A, EPA and DHA was accomplished using a Phenomenex© Security Guard® C18 column (4×3 mm ID, Phenomenex, Torrance, CA) and a Waters™ Xbridge© C18 3.5 μm column (2.1 mm×100 mm, Waters Corporation, Milford, MA). The mobile phase consisted of 5 mM ammonium formate and 0.1% formic acid as component A and acetonitrile as component B. A linear gradient was run as follows: 0 min 10% B; 1 min 10% B, 5 min 90% B; 10 min 90% B; 10.1 min 10% B at a flow rate of 0.2 mL/min, with an oven temperature at 40° C. The total run time was 15 min per sample. The MS/MS analysis was performed using a QTRAP mass spectrometer model API 5500 system from Applied Biosystems/MDS SciEx in negative ionization mode equipped with Turbo Ion Spray® (TIS) device (Applied Biosystems, Foster City, CA, USA). The MRMs were: MRM1 (355.11-219.10) and MRM2 (355.11-82.90) for gingerenone A; MRM1 (301.14-217.00) and MRM2 (301.14-255.20) for EPA and MRM (327.30-283.20) for DHA. The TIS instrumental source settings for temperature, curtain gas, ion source gas 1 (nebulizer), ion source gas 2 (turbo ion spray) and ion spray voltage and entrance potential were 400° C., 25 psi, 60 psi, 60 psi and −4500 V and −10V, respectively. For gingerenone A TIS compound parameter settings (declustering potential, collision energy and cell exit potential) for MRM1 were −105 V, −20 V and −11 and for MRM2 were −105 V, −32 V and −7. For EPA, the TIS compound parameter settings (declustering potential, collision energy and cell exit potential) for MRM1 were −80 V, −34 V and −11 and for MRM2 were −80 V, −8 V and −13. For DHA, the TIS compound parameter settings (declustering potential, collision energy and cell exit potential) for MRM was −135 V, −14 V and −13 V. The relative quantitation of gingerenone A, EPA and DHA was accomplished by using the area under the curves. The data were acquired and analyzed using Analyst version 1.4.2 (Applied Biosystems). For plasma samples, 120 μL of acetonitrile was added to 40 μL of plasma and vortex mixed. The sample was then centrifuged at 4° C. for 5 min at 17,000×g and 120 μL was removed and stream dried under nitrogen. It was resuspended in 30 μl of acetonitrile, vortex mixed and then centrifuged at 17,000×g for 5 min. Then 25 μL was removed and placed in an autosampler vial for analysis and 10 μl was injected.

Example 1

Prodrug Synthesis

Figure 2:
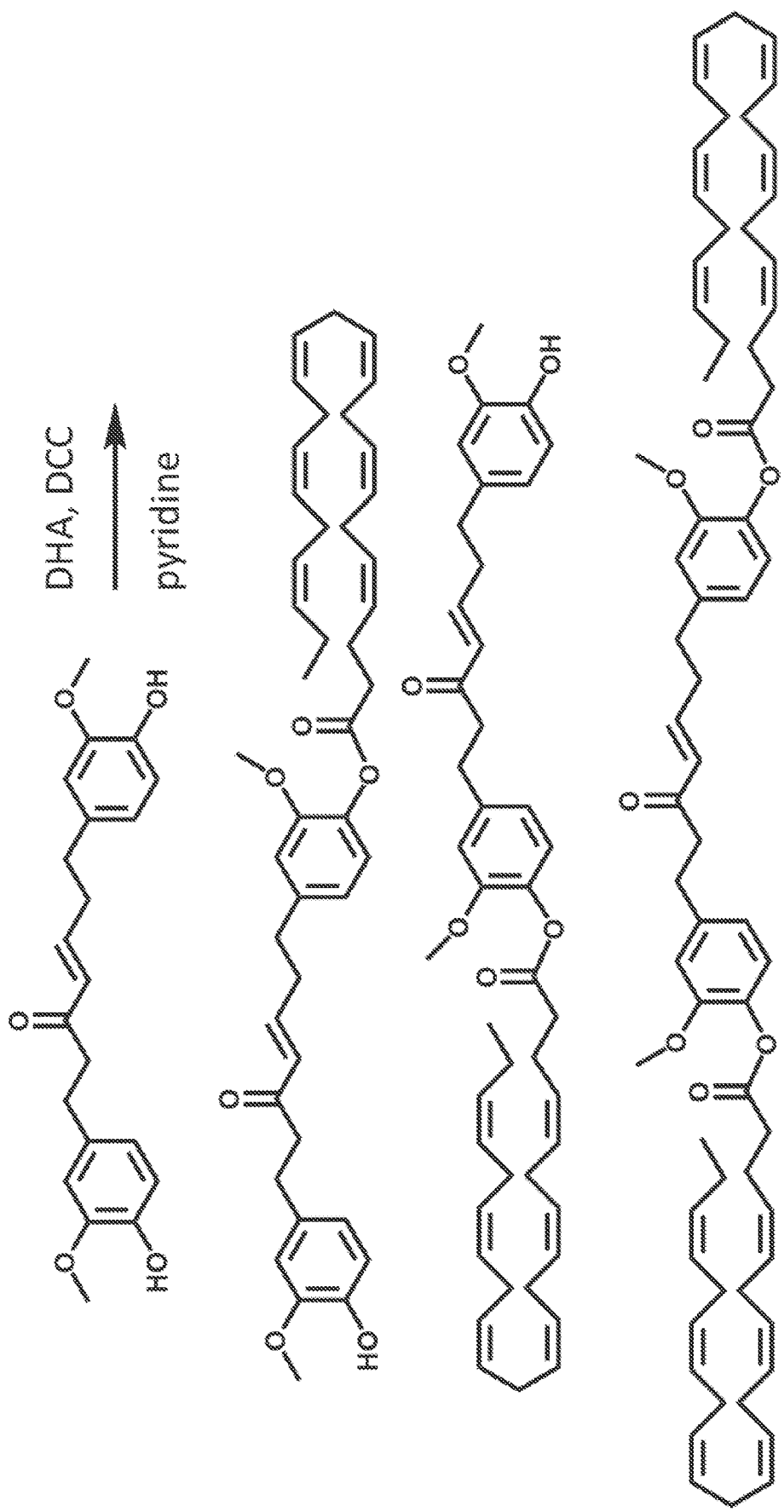
FIG. 2 is an exemplary scheme for synthesizing a gingerenone A prodrug comprising two docosahexaenoic acid (DHA) ester groups.

Prodrugs where $R^1$ and $R^2$ Correspond to EPA or DHA:
Synthesis 1: To a solution of EPA or DHA (1 mol equivalent) in 5 ml of anhydrous pyridine is added DCC (dicyclohexyl carbodiimide) (87 mg; 1.5 mol equivalent) (FIGS. 1 and 2, respectively). The solution is stirred for 5 hours, then a solution of gingerenone A (100 mg; 0.280 mmol) in 1 ml of pyridine is added. The reaction is allowed to proceed overnight, and then diluted with diethyl ether and washed with water, then 10% CuSO4, then brine. It is dried over sodium sulfate and then evaporated. The mixture of esters is separated by flash chromatography and characterized by NMR and LC-MS.

Figure 3:
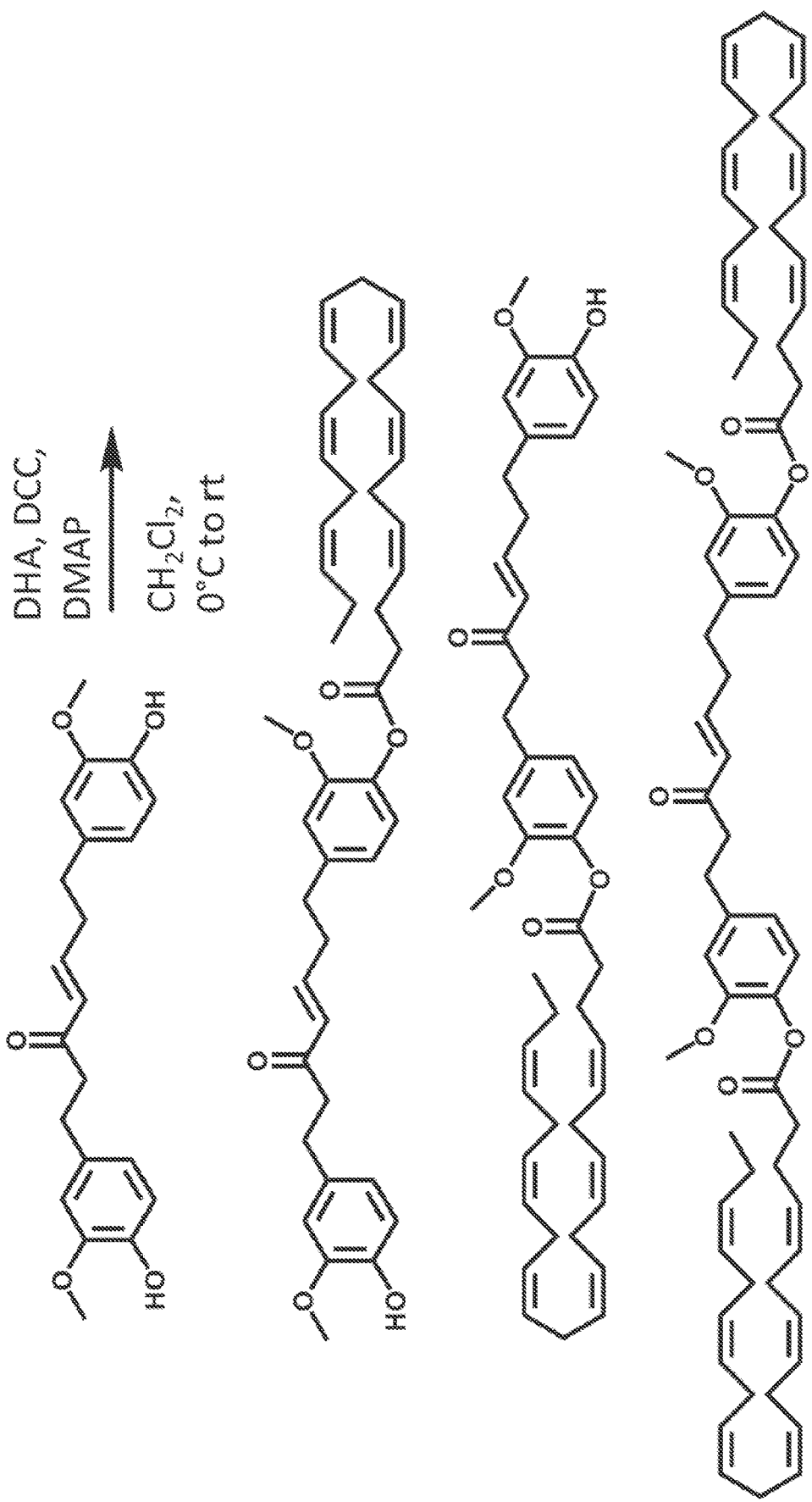
FIG. 3 is another exemplary scheme for synthesizing a gingerenone A prodrug comprising two eicosapentaenoic acid (EPA) ester groups.
Figure 4:
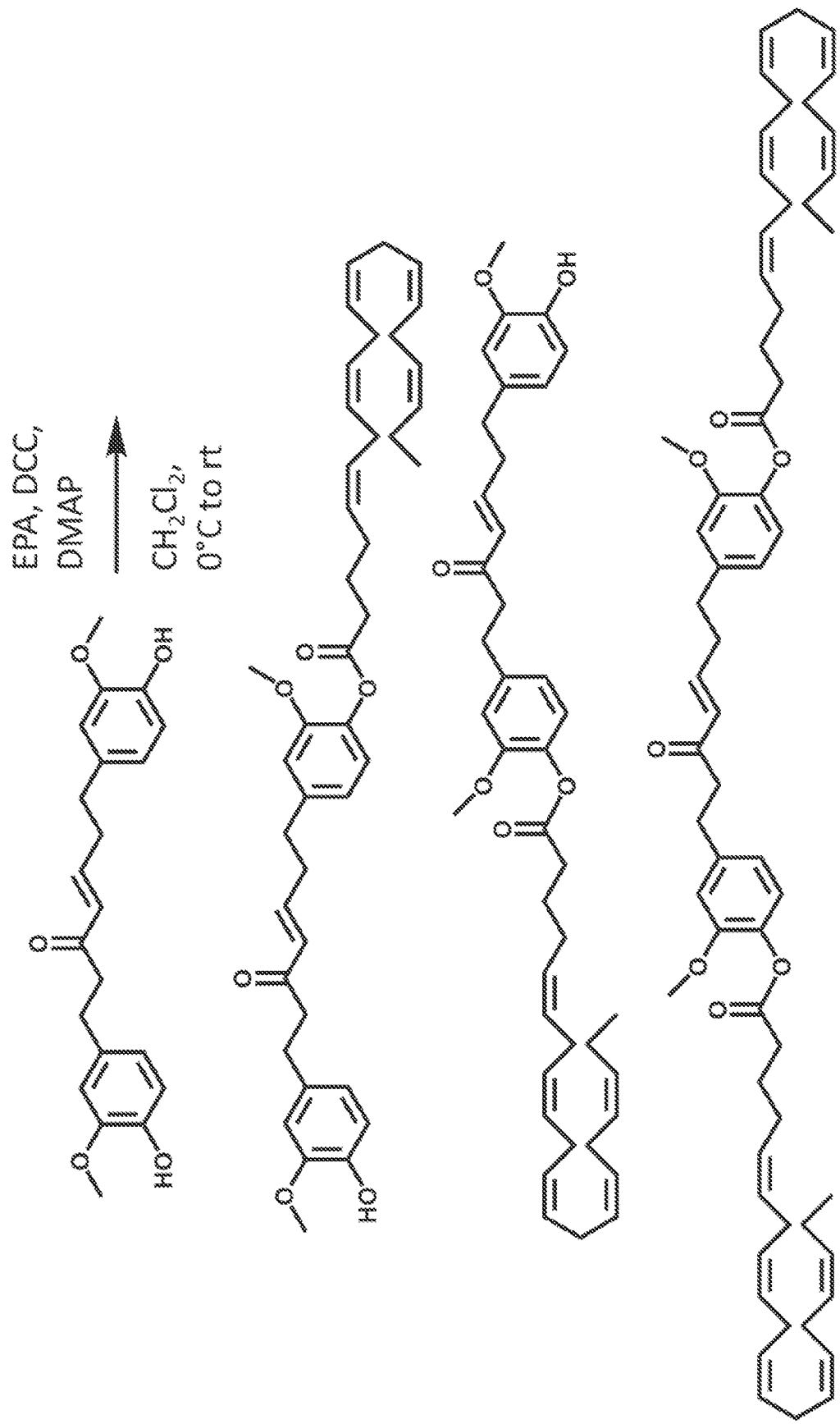
FIG. 4 is another exemplary scheme for synthesizing a gingerenone A prodrug comprising two docosahexaenoic acid (DHA) ester groups.

Synthesis 2: To a solution of Gin A (100 mg) in 3 ml of dichloromethane was added a solution of DHA (221 mg; 2.4 equiv.) in 2 ml of dichloromethane, followed by 4-dimethylaminopyridine (6.86 mg; 0.2 equiv.) (FIG. 3). The mixture was cooled to 0° C., then DCC (185 mg; 3.2 equiv.) was added. The reaction was stirred at 0° C. for 10 minutes, then at room temperature overnight. The mixture was concentrated to about 1 ml, then purified on a 24 g silica column (RediSep® Rf flash cartridge) using 7% ethyl acetate/hexane to elute the product. All fractions containing the di-ester product (Rf=0.45, visualized with UV and with sulfuric acid spray plus heating) were combined and repurified on a 40 g silica column (RediSep® Rf flash cartridge), using a gradient of 7% to 20% ethyl acetate in hexane to elute 23 mg of pure GinA-di-DHA ester (81% yield). The same method was used to synthesis a GinA-di-EPA ester (FIG. 4).

Gingerenone A Selective Procedures

Figure 5A:
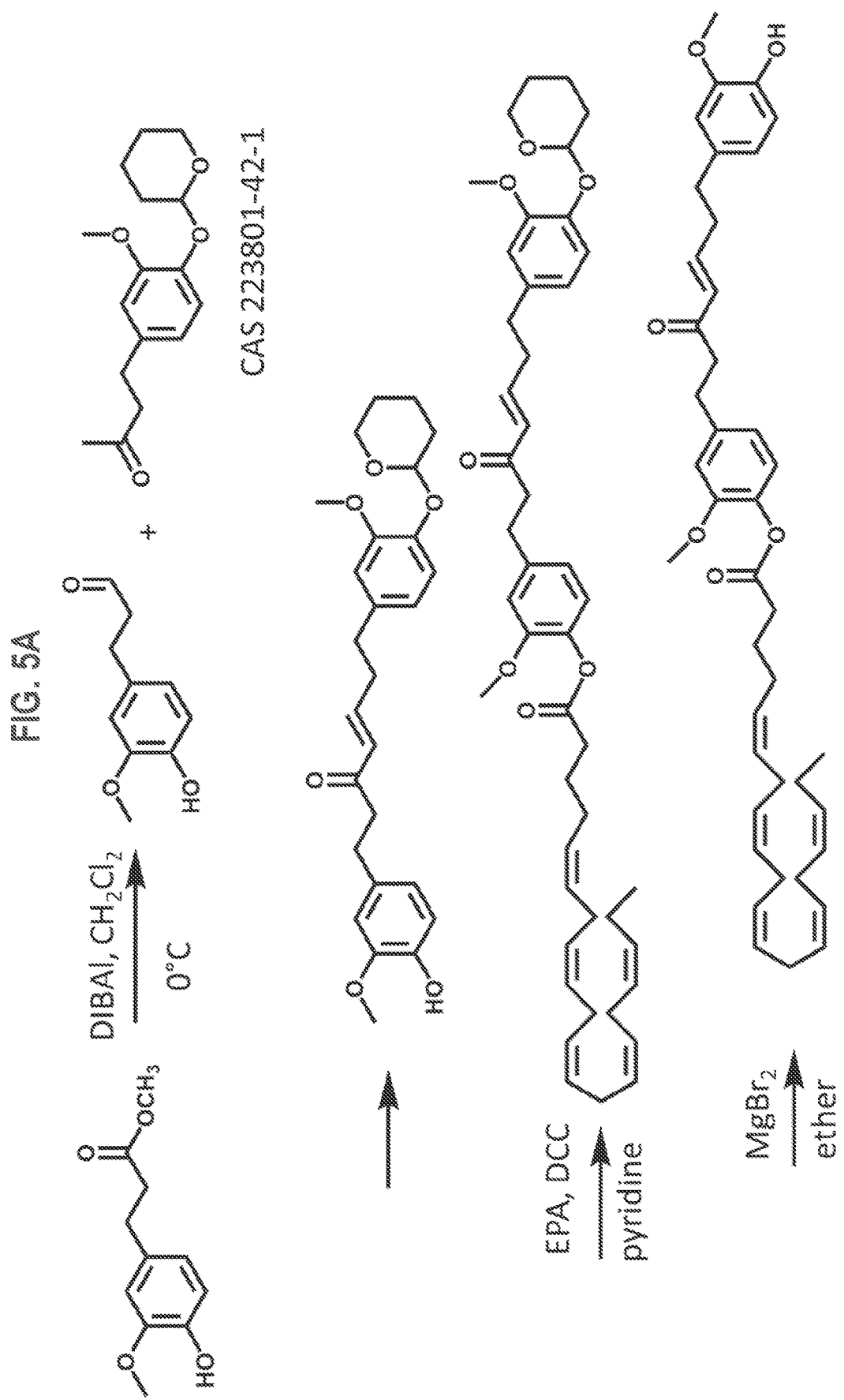
FIGS. 5A and 5B are exemplary schemes for synthesizing a gingerenone A prodrug comprising a single EPA ester group.
Figure 6A:
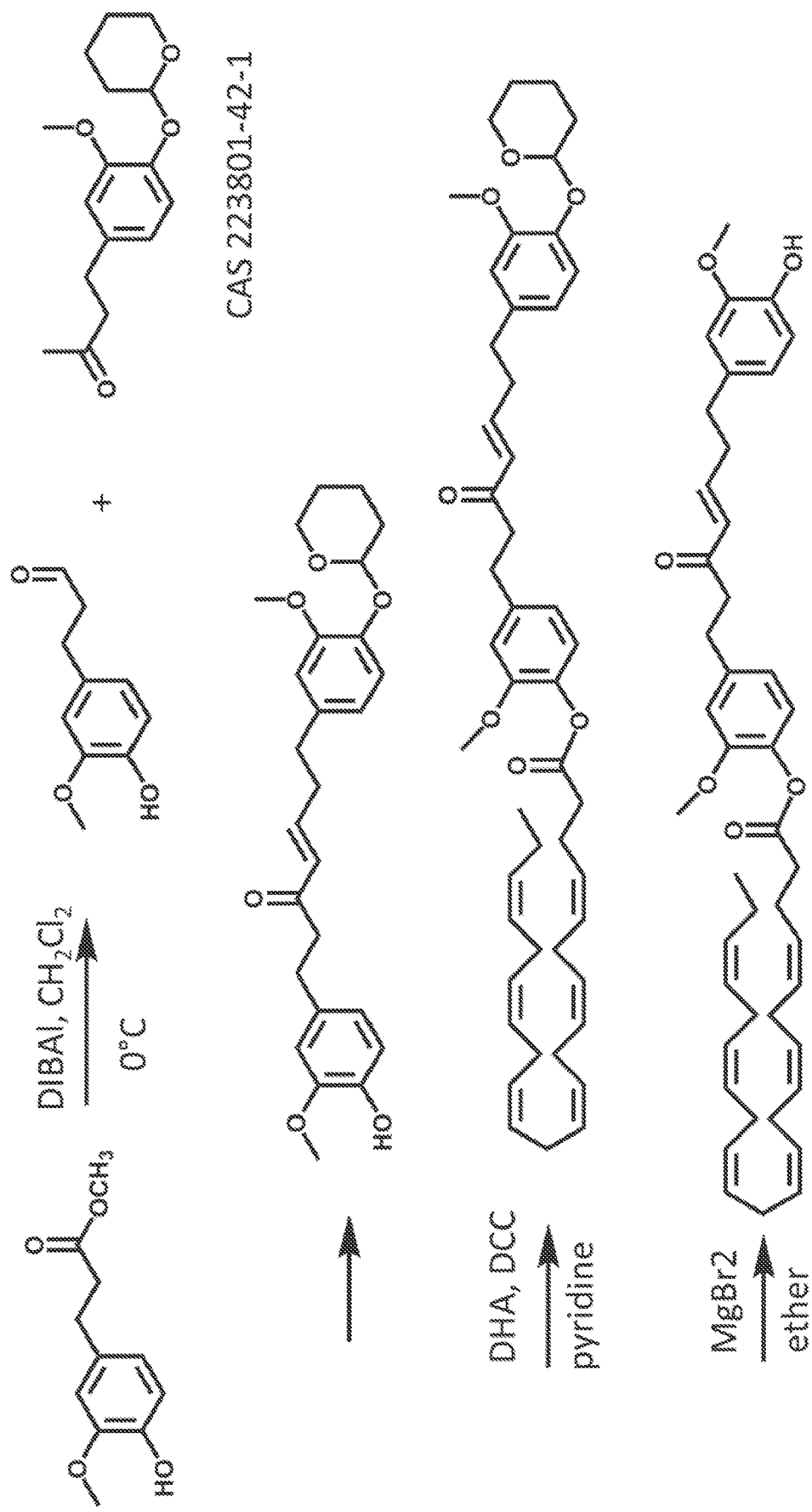
FIGS. 6A and 6B are exemplary schemes for synthesizing a gingerenone A prodrug comprising a single DHA ester group.

Procedure 1: To a solution of methyl 3-(4-hydroxy-3-methoxyphenyl)propanoate (100 mg; 0.476 mmol) in 5 ml of anhydrous dichloromethane at 0° C. is added a 1M solution of diisobutylaluminum hydride in dichloromethane (524 μL; 1.1 mol equivalent) dropwise. The reaction is allowed to reach room temperature as it progresses to completion as indicated by TLC (FIGS. 5A and 6A). Then a solution of 4-[3-methoxy-4-(oxan-2-yloxy)phenyl]butan-2-one (159 mg; 1.2 mol equivalent) in 2 ml dichloromethane is added, and the reaction is stirred overnight. Then it is diluted with ether and washed with saturated ammonium chloride, then water and then brine. It is dried over sodium sulfate and evaporated. The mono-THP Gin A product is isolated by flash chromatography.

To a solution of EPA or DHA (1 mol equivalent) in 3 ml of anhydrous pyridine is added DCC (36 mg; 1.5 mol equivalent) (FIGS. 5A and 6A, respectively). The solution is stirred for 5 hours, then a solution of mono-THP-gingerenone A (50 mg; 0.113 mmol) in 1 ml of pyridine is added. The reaction is allowed to proceed overnight, and then it is diluted with diethyl ether and washed with water, then 10% CuSO4, then brine. It is dried over sodium sulfate and then evaporated. The product ester is separated by flash chromatography and then deprotected in 10 ml of anhydrous diethyl ether with 3 equivalents of $MgBr_2$ for 5 hrs. The reaction is washed with water, then brine and then dried over sodium sulfate and evaporated. Isolation of the mono ester product is achieved with flash chromatography. It is characterized using NMR and LC-MS.

The diester (mixed or bis-) is prepared in dichloromethane using DCC from the mono ester in dichloromethane using DCC as above.

Figure 5B:
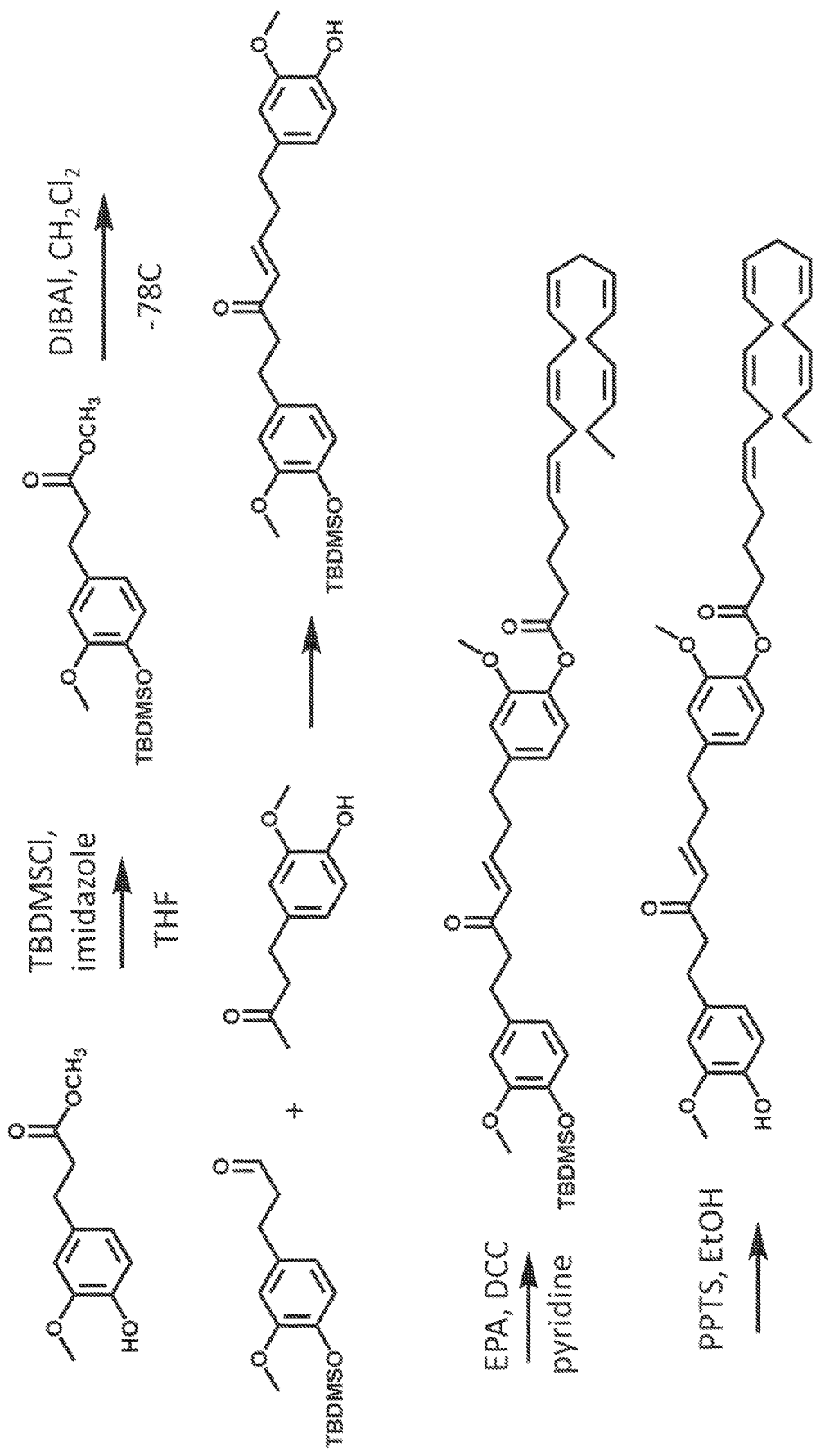
Figure 6B:
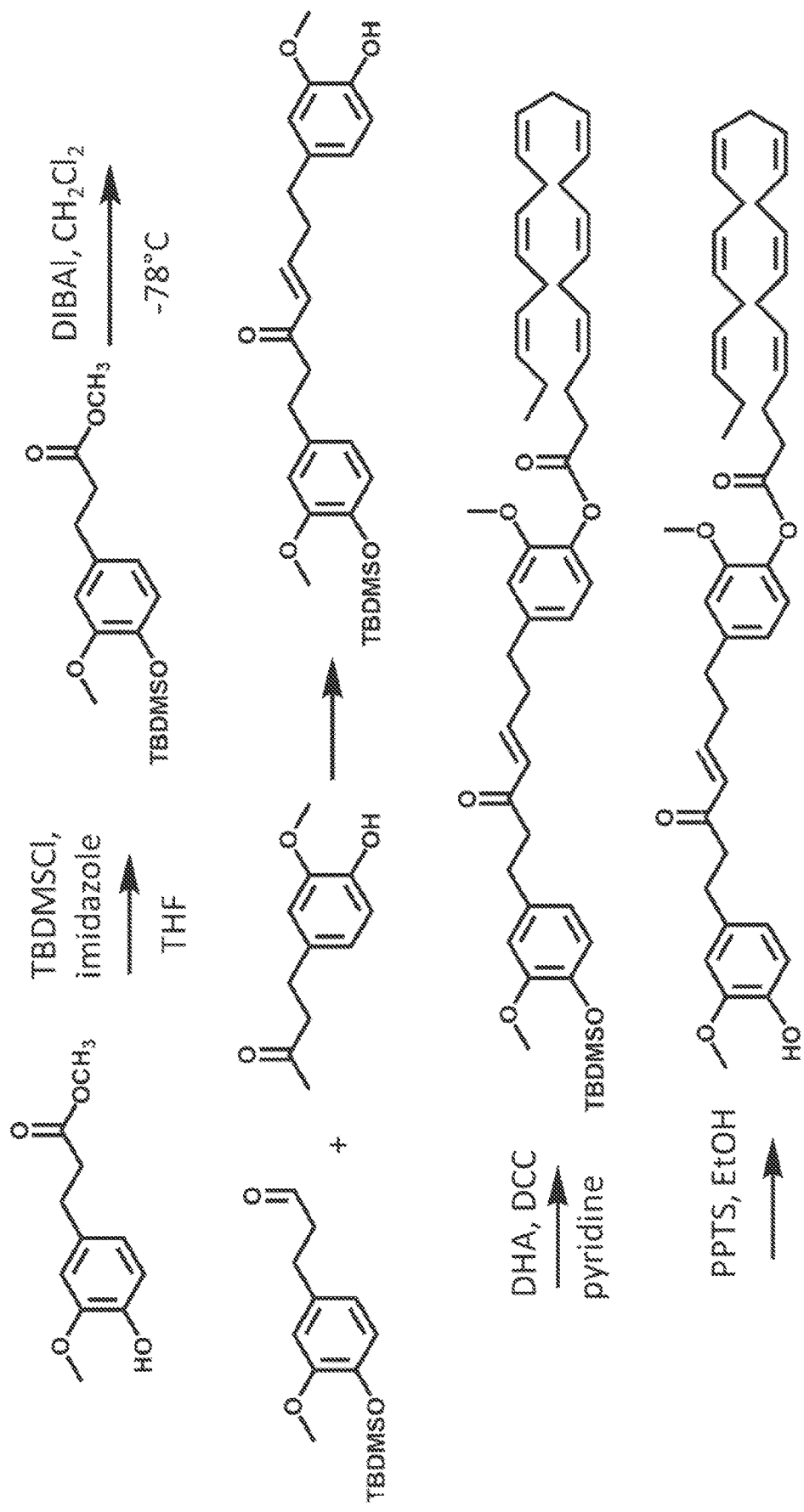

Procedure 2: To a solution of methyl 3-(4-hydroxy-3-methoxyphenyl)propanoate (1 g; 4.76 mmol) in 5 ml of anhydrous dimethylformamide at 0° C. is added imidazole (486 mg; 1.5 mol equivalent) followed by (tert-butyldimethylsilyl chloride (714 mg; 1.5 mol equivalent) (FIGS. 5B and 6B). The reaction is allowed to reach room temperature as it progresses to completion as indicated by TLC. Then it is diluted with ether and washed with water and then brine.

It is dried over sodium sulfate and evaporated. The mono-TBDMS product is isolated by flash chromatography.

To the mono-TBDMS compound (250 mg; 0.781 mmol) in 3 ml of anhydrous dichloromethane at 0° C. is added a 1M solution of diisobutylaluminum hydride in dichloromethane (859 µl; 1.1 mol equivalent) dropwise. The reaction is allowed to reach room temperature as it progresses to completion as indicated by TLC. Then a solution of vanillylacetone (230 mg; 1.2 mol equivalent) in 2 ml dichloromethane is added, and the reaction is stirred overnight. Then it is diluted with ether and washed with saturated ammonium chloride, then water and then brine. It is dried over sodium sulfate and evaporated. The mono-TBDMS Gin A product is isolated by flash chromatography.

A solution of EPA or DHA (1 mol equivalent) in 3 ml of anhydrous pyridine is added DCC (36 mg; 1.5 mol equivalent) (FIGS. 5B and 6B, respectively). The solution is stirred for 5 hours, then a solution of mono-TBDMS-gingerenone A (50 mg; 0.106 mmol) in 1 ml of pyridine is added. The reaction is allowed to proceed overnight, and then it is diluted with diethyl ether and washed with water, then 10% $CuSO_4$, then brine. It is dried over sodium sulfate and then evaporated. The product ester is separated by flash chromatography and then deprotected in 10 ml of anhydrous ethanol with pyridinium para-toluenesulfonic acid (565 g; 20% mol) for 3 hrs. The reaction is washed with water, then brine and then dried over sodium sulfate and evaporated. Isolation of the mono ester product is achieved with flash chromatography. It is characterized using NMR and LC-MS.

Figure 7:
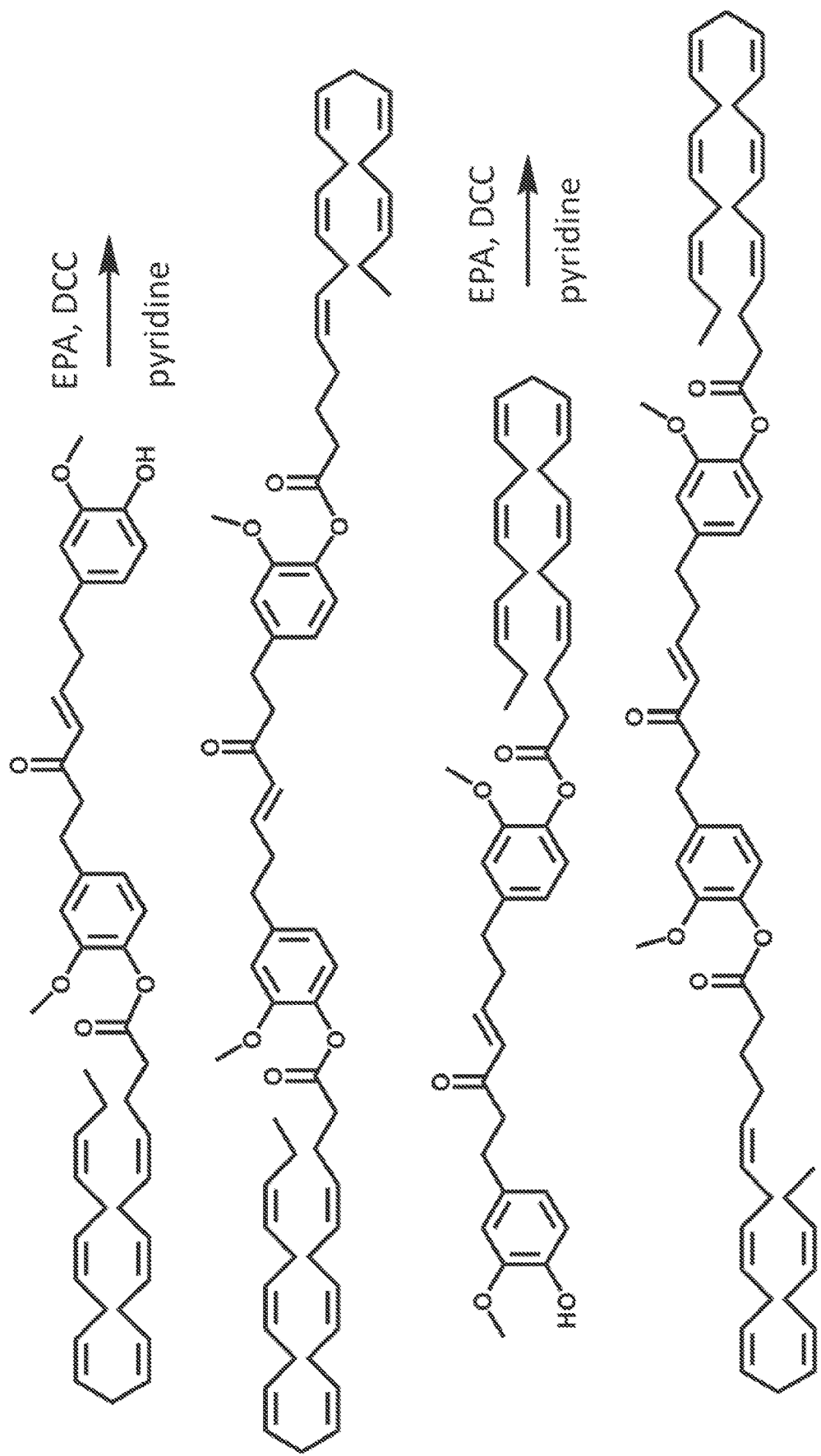
FIG. 7 shows exemplary schemes for synthesizing gingerenone A prodrugs comprising one EPA ester group and one DHA ester group.

The diester (mixed or bis-) is prepared in dichloromethane using DCC from the mono ester in dichloromethane using DCC as above (FIG. 7).

Example 2

Senolytic Properties in Ginger Extract

Figure 8A:
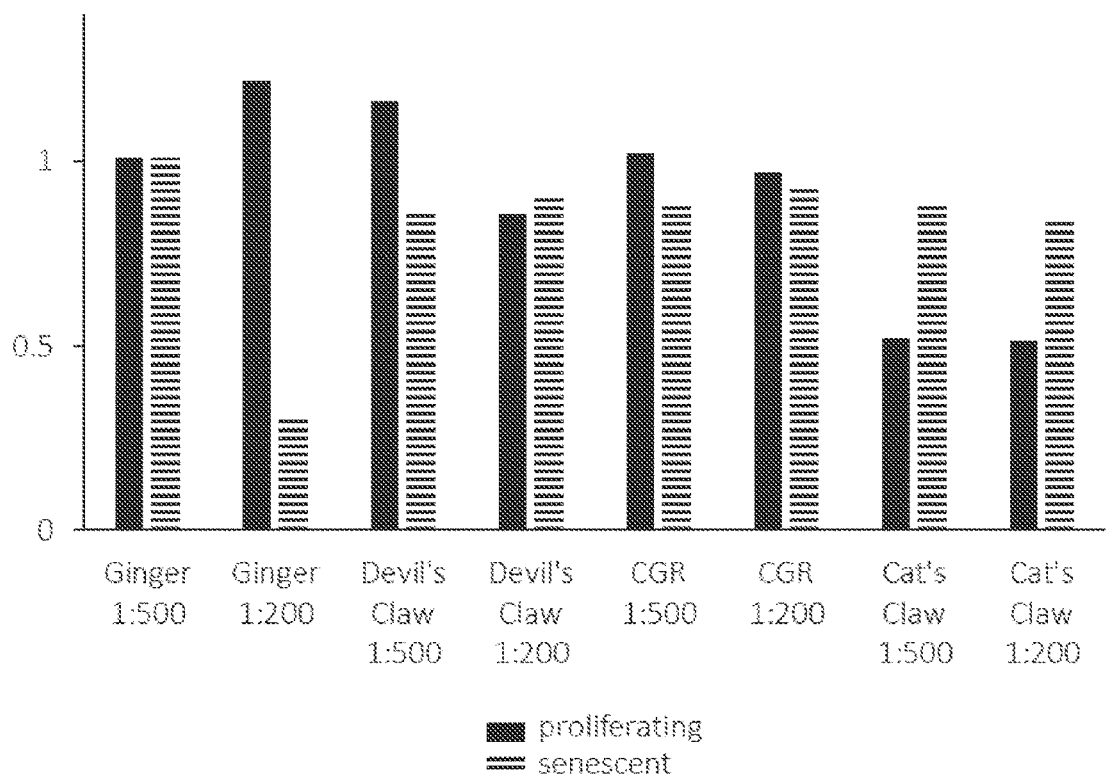
FIGS. 8A and 8B are bar graphs showing that only ginger extract 1:200 dilution markedly decreased senescent cell viability compared to other extracts.
Figure 8B:
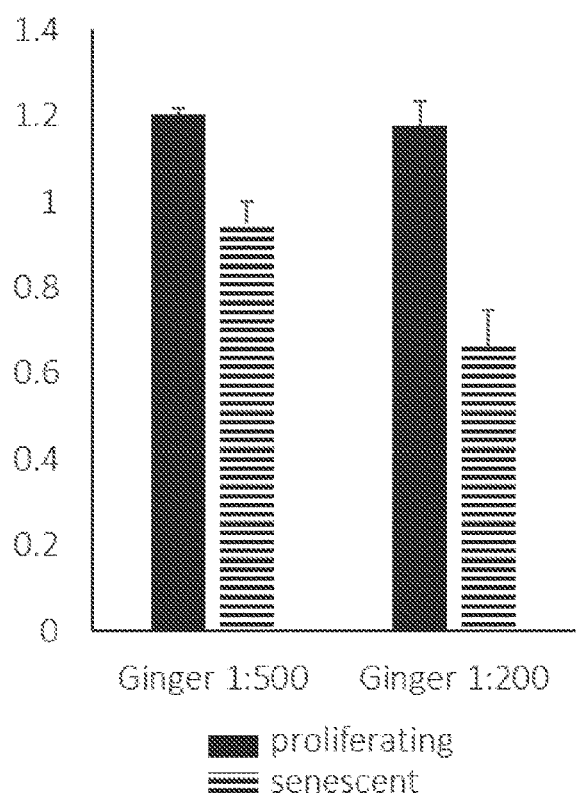
Figure 9A:
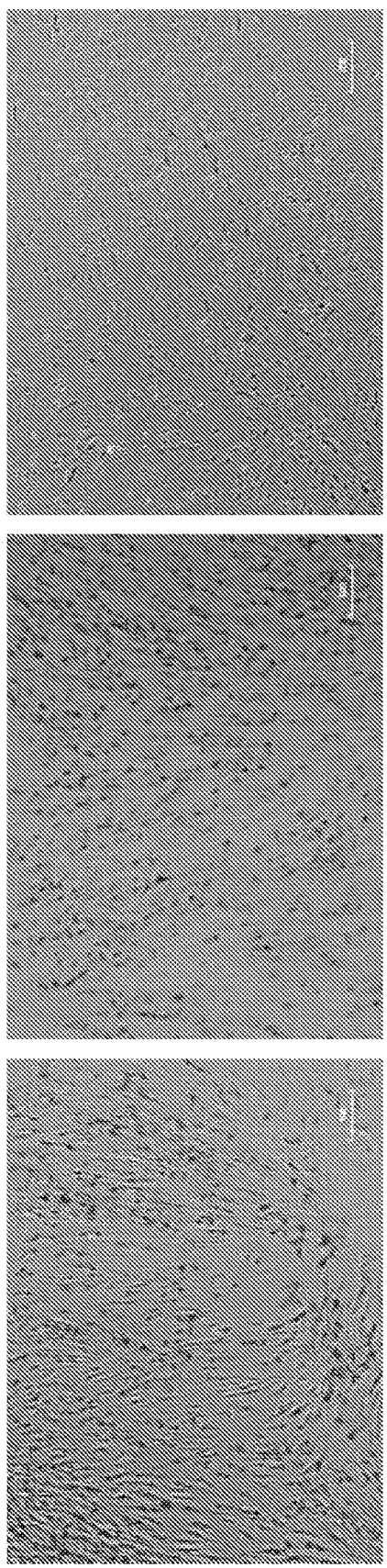
FIGS. 9A and 9B are images showing senescence-associated β-galactosidase (SA-βGal) staining of the cells prepared with ginger extract in FIG. 6A; staining was performed at 24 h (FIG. 9A) and 72 h (FIG. 9B).
Figure 9B:
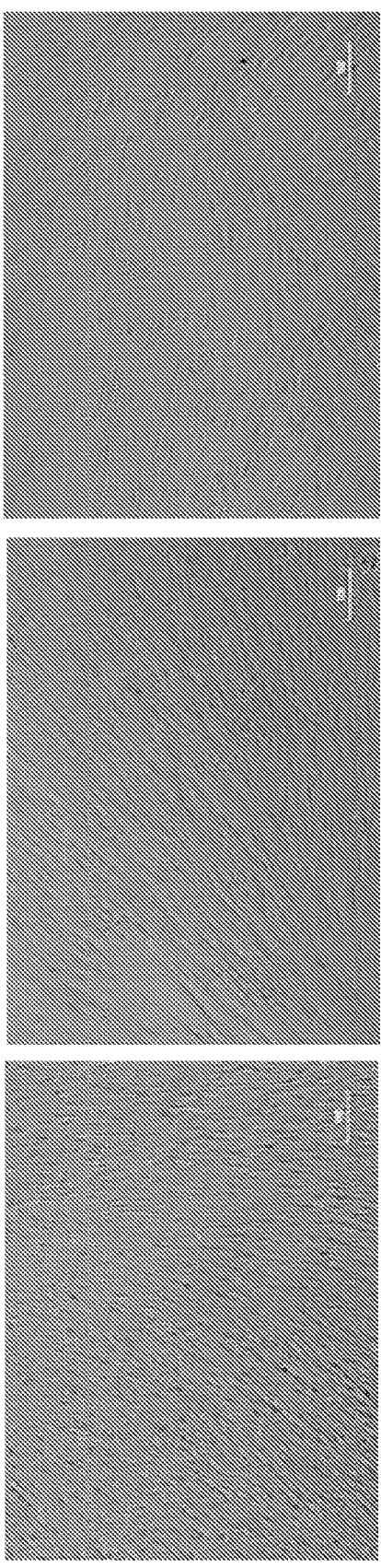

Four plant extracts were screened for senolytic activity, including extracts from *Harpagophytum procumbens* (Devil's Claw), *Uncaria tomentosa* (Cat's Claw), *Zingiber officinale* Rosc. (ginger) and Canadian Golden Rod. These extracts were screened using the MTT cell viability assay with WI-38 fibroblasts. To avoid nonspecific effects, proliferating cells and cells rendered senescent by exposure to ionizing radiation (IR) were used as a screening system. IR senescence was triggered by exposure to 10 Gy followed by culture for an additional 10 days, whereupon cells were treated with the indicated extracts and dilutions for 24 h (FIG. 8A). In FIG. 8B, the impact on ginger extract on proliferating and senescent cells on cell survival was assessed by the MTT cell viability assay. Data are represented as the mean and standard errors from biological replicates [senescent n=9 and proliferating (1:500 (n=4) and 1:200 (n=7), (***p<0.005)]. Cells that were prepared as described for FIG. 6A were treated with ginger extract for 24 h (FIG. 9A) or 72 h (FIG. 9B) followed by senescence-associated β-galactosidase (SA-βGal) staining.

As shown in FIGS. 8A and 8B, only ginger extract (1:200 dilution) markedly decreased senescent cell viability compared to other extracts. Interestingly, incubation with extracts from *Uncaria tomentosa* decreased cell viability in proliferating cells but had no effects on IR-induced senescent cells (FIG. 8A). Incubation with ginger extracts displayed senolytic activity (FIG. 8B) and decreased SA-βGal activity at 24 and 72 h (FIGS. 9A and 9B, respectively), suggesting a possible shift in senescence traits. While this effect could be due to a reduction in the number of senescent cells, it could also result from the inhibition of SA-βGal activity by ginger extracts.

Example 3

Gingerenone A Activity

Figure 10A:
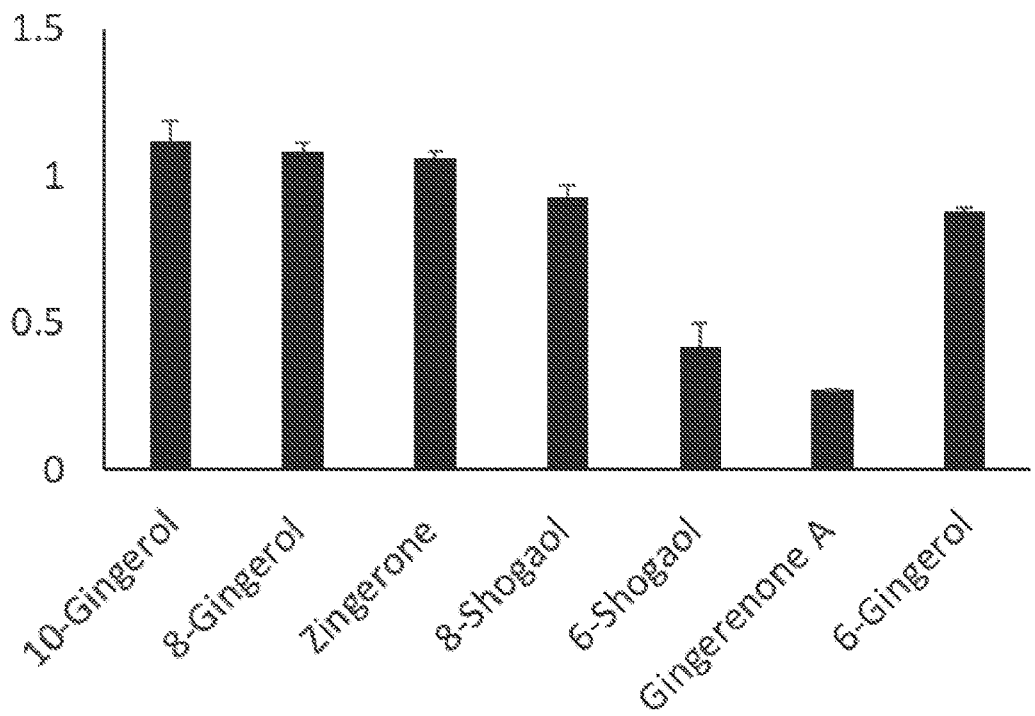
Figure 10B:
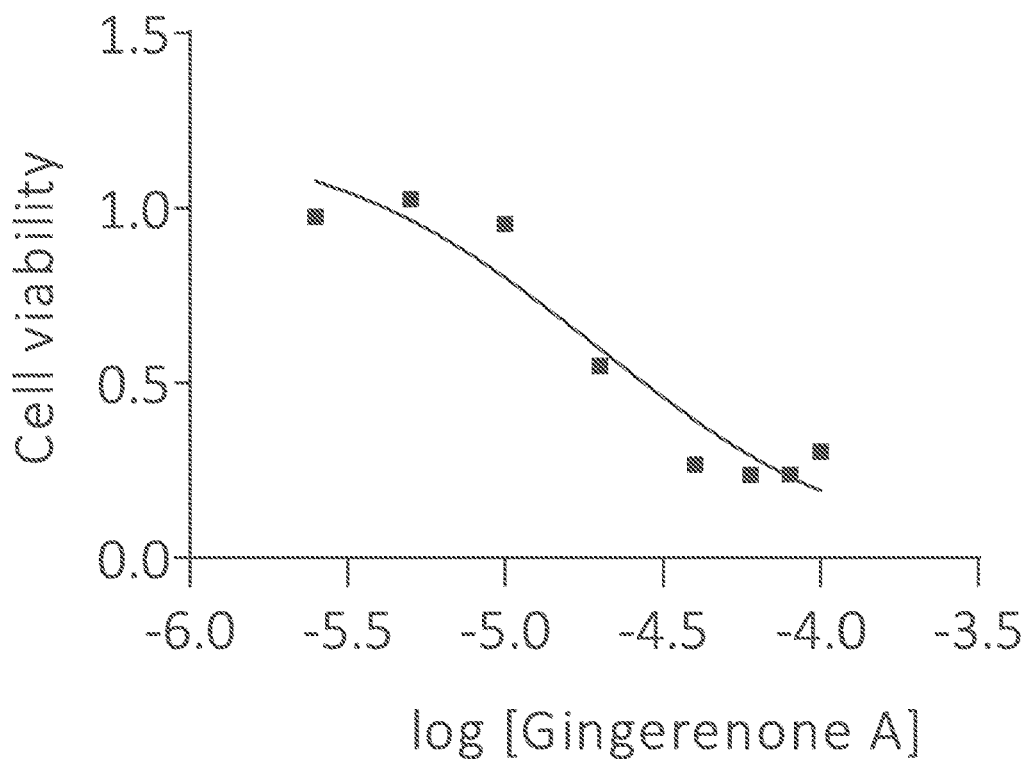

A candidate approach was used to identify the active senolytic component within the ginger extract. WI-38 fibroblasts were rendered senescent by exposure to ionizing radiation (IR, 10 Gy) and cultured for an additional 10 days. Cells were then treated with the ginger components at 100 µM, with 6-shogaol at 3.6 µM, 8-shogaol at 33 µM and 6-gingerol at 20 µM for 72 h, and then cell survival was assessed by the MTT cell viability assay. Data represent the means and standard error from three biological replicates. The major components of ginger extract, namely 6-gingerol, 8-gingerol, 10-gingerol, 6-shogaol, 8-shogaol, gingerenone A, and zingerone, were screened for their ability to selectively decrease cell viability of senescent cells using the MTT assay (FIG. 10A). Dose-response effect of gingerenone A [2.5-100 µM] treatments for 72 h on senescent cell viability 10-days post-irradiation. Among the active components, only 6-shogaol and gingerenone A displayed senolytic activity. The $IC_{50}$ of gingerenone A was determined to be 19.6±2.1 µM ($r^2$=0.9214) (FIG. 10B). Gingerenone A was incubated with cells that were either proliferating (grey) or senescent (red) as explained in panel (A) for 48 h at 10 and 20 µM (*p=0.04). Data represent the means and standard error from eight biological replicates. Treatment with 20 µM gingerenone A resulted in a significant decrease in senescent cell viability relative to proliferating cells (p=0.04) (FIG. 10C).

Figure 11C:
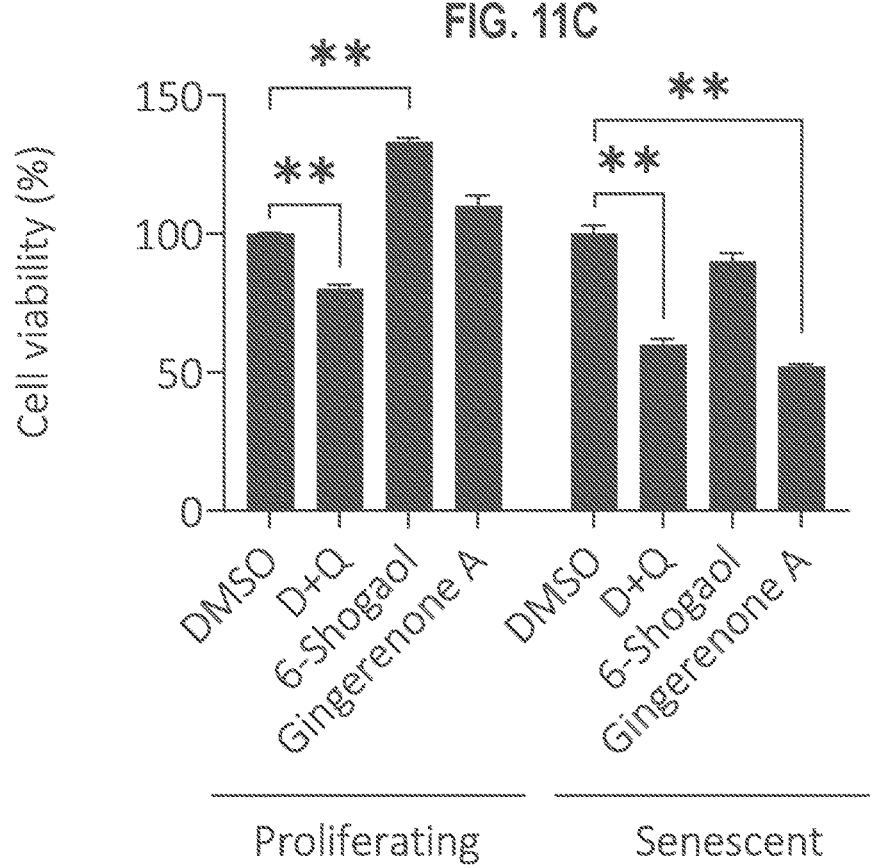

The cytotoxic action of gingerenone A was compared with that of the known senolytic D+Q. WI-38 fibroblasts were either left untreated (proliferating) or rendered senescent by exposure to ionizing radiation (IR, 10 Gy) and cultured for an additional 10 days. Cells were then treated with either vehicle (DMSO), dasatinib (250 nM) and quercetin (10 µM) (D+Q), gingerenone A (20 µM), or 6-shogaol (72.4 nM) and incubated for 24 h (FIG. 11A) or 48 h (FIG. 11B), whereupon cell viability was assayed by MTT analysis [proliferating (grey) and senescent (red)]. Data in the graphs of FIG. 9C represent the means and standard error from three biological replicates. Micrographs are representative of three biological replicates. Forty-eight hours after treatment, D+Q showed a decrease in senescent cell viability, with a moderate toxic effect on proliferating cells (FIGS. 11B, 11C). Interestingly, treatment with 72.4 nM of 6-shogaol induced a significant increase in the number of proliferating cells (FIG. 11C) and showed a moderate degree of cell death in senescent cells. Treatment with gingerenone A did not show any significant effect on the proliferation of non-irradiated cells, however it significantly decreased senescent cell viability, and showed a higher selectivity compared to D+Q.

Figure 12A:
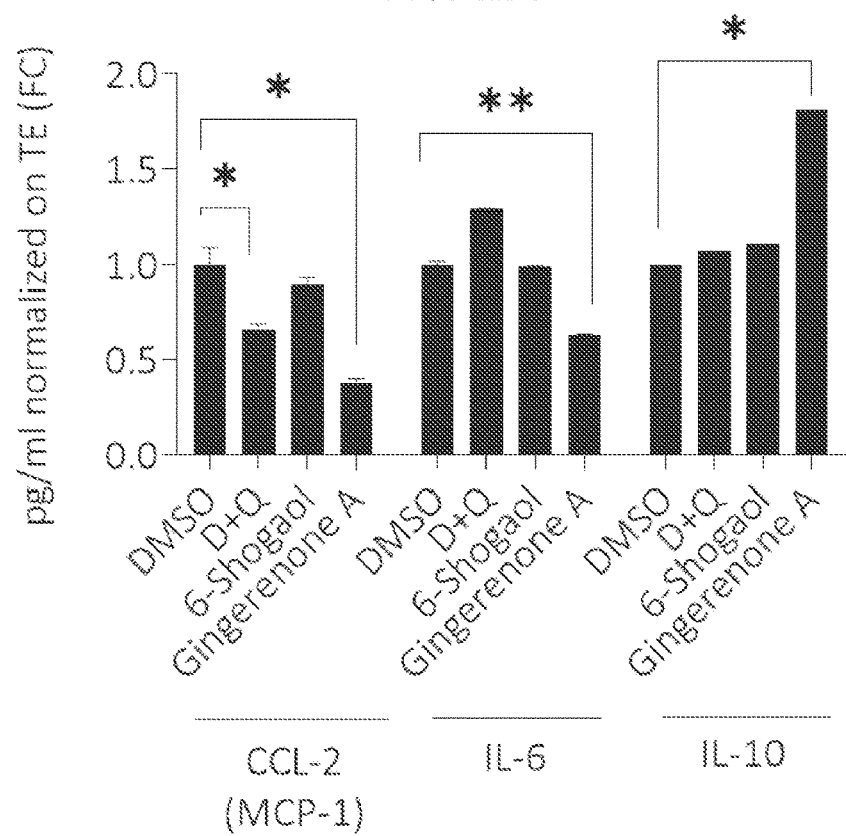
FIGS. 12A and 12B show effects of gingerenone A, 6-shogaol and D+Q on cytokines and chemokines that are known to be part of the senescence-associated secretory phenotype (SASP).
Figure 12B:
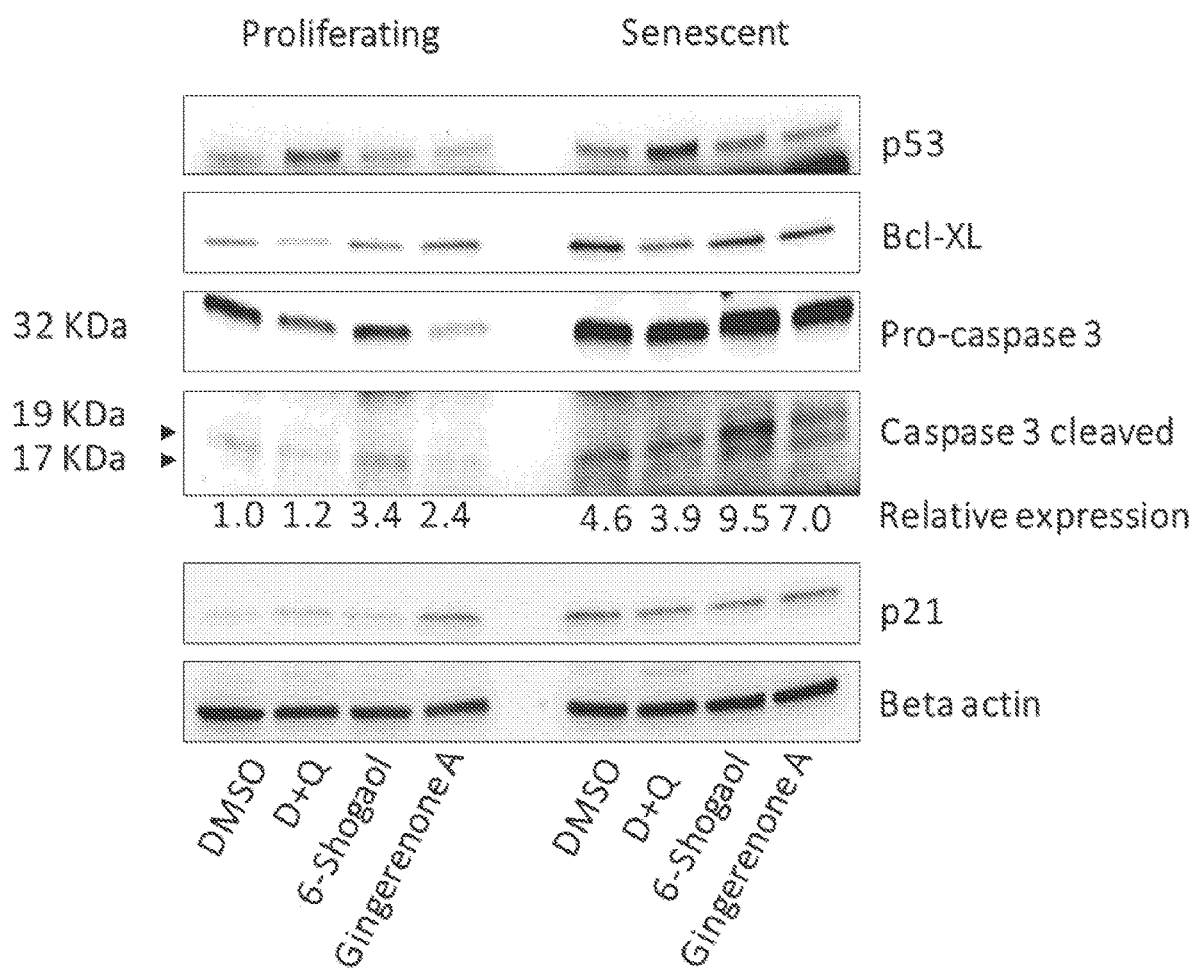

The effects of gingerenone A, 6-shogaol and D+Q on cytokines and chemokines that are known to be part of the senescence-associated secretory phenotype (SASP) were tested. WI-38 fibroblasts were rendered senescent by exposure to ionizing radiation (IR, 10 Gy) and cultured for an additional 10 days. Cells were then treated with gingerenone A (20 µM) and 6-shogaol (72.4 nM) and incubated for 24 h. CCL-2 (MCP-1) and IL-10 were measured using the Bio-plex (Multiplex); IL6 was measured using Quantikine IL-6 (R&D) (FIG. 12A). Data were normalized to cell number/total protein content. Data in graphs represent the means and standard error from three biological replicates. FIG. 12B shows Western blot analysis of the proteins after treating proliferating and senescent fibroblasts (as shown in FIG. 12A) for 48 h with the drugs indicated. Ratios of cleaved pro-caspase 3 to total caspase 3, normalized to ACTB levels, are shown as relative to control proliferating cells. Cytokines (FIG. 13A) and chemokines (FIG. 13B) were measured using the V-plex panel (MSD) after treatment for 24 h with the indicated drugs. Relative secretion was measured as pg/ml vs control normalized on TE. Data in the graphs represent the means and standard error from three biological replicates.

Figure 13B:
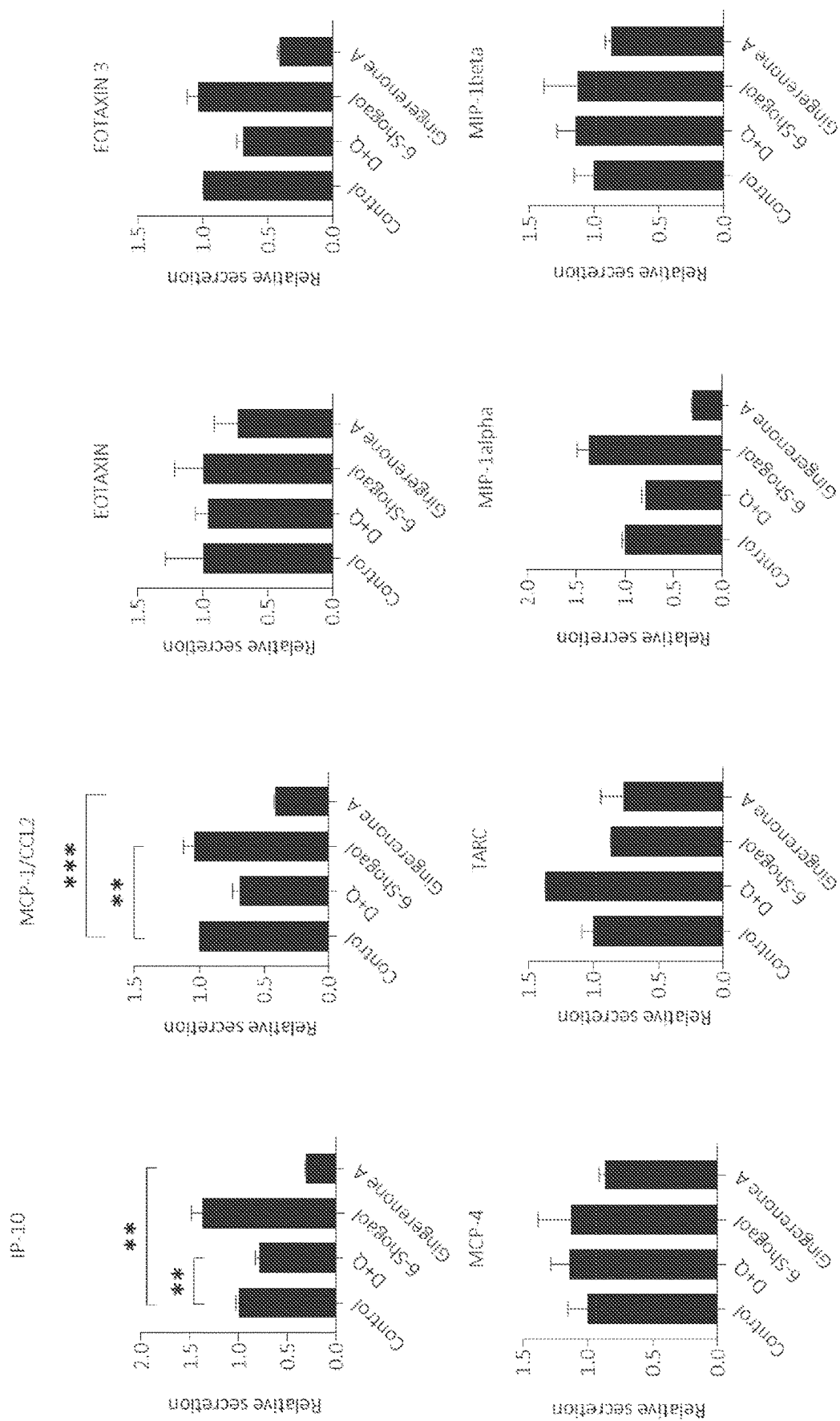

Treatment with gingerenone A reduced the secreted levels of the pro-inflammatory factors IL-6, CCL2 (MCP-1) (FIGS. 12A, 13A, 13B) and interferon γ-induced protein 10 (IP-10) (FIG. 13B) and increased the levels of the anti-inflammatory cytokines IL-10 and IL-13 (FIGS. 12A, 13A). However, treatment with gingerenone A also increased the levels of pro-inflammatory cytokines IL-8 and IL-10 (FIG. 13A). While treatment with D+Q resulted in a similar reduction in secreted MCP-1 and IP-10 levels, it also reduced the levels of IL-10 and IL-8 (FIG. 13A), with enhanced secretion of the pro-inflammatory cytokines IL-6, IL-4 and IFN-G (IFNγ) (FIG. 13A). Conversely, treatments with 6-shogaol did not induce major changes in any of the cytokines and chemokines measured at the tested concentration, suggesting that 6-shogaol does not have senomorphic effects compared to gingerenone A.

These results suggest that the senomorphic effects of gingerenone A and D+Q occur through somewhat different mechanisms. Of note, while IL-6, IL-8 and MCP-1 (CCL2) had similar results across different assay platforms, IL-10, which showed an increase with gingerenone A when measured by multiplex ELISA (FIG. 12A), was unchanged in the V-Plex (FIG. 13A). Whether this discrepancy results from the different antibodies used in the different platforms remains unknown.

To determine whether gingerenone A and 6-shogaol might influence the apoptotic pathway, their effect on the levels of cleaved caspase-3 (pro-apoptotic marker), and Bcl-XL (anti-apoptotic protein) (FIG. 12B) was tested. Treatment with D+Q, but not with gingerenone A or 6-shogaol, increased p53 levels in both proliferating and senescent cells. However, D+Q, gingerenone A, and 6-shogaol all reduced the expression of the anti-apoptotic protein Bcl-XL in senescent cells (FIG. 12B, right). Interestingly, both gingerenone A and 6-shogaol induced an increase in the levels of the pro-apoptotic protein cleaved caspase-3 in senescent cells. These results indicate that gingerenone A may induce senescent-cell death through caspase-3 and independently of p53.

In summary, gingerenone A and 6-shogaol were identified as active components in ginger extract, with gingerenone A showing higher selectivity for eliminating senescent cells when compared to a known senolytic cocktail (D+Q). The senomorphic effects of gingerenone A and 6-shogaol and the secretion of SASP factors by senescent cells were evaluated. The activation of the SASP comprises a range of chemokines, pro-inflammatory cytokines, growth factors and matrix-remodeling enzymes that affect their microenvironment. The senomorphic effects of gingerenone A were demonstrated by the reduced secretion of pro-inflammatory factors, including IL-6, IP-10 and MCP-1, and the increase in anti-inflammatory cytokines IL-10 and IL-13. However, gingerenone A was also found to increase the secretion of potent pro-inflammatory SASP cytokines (IL-1B and IL-8) in senescent cells. The divergence of IL-6 and IL-8 secretion with gingerenone A treatment suggests that the mechanism is independent of IL-1A (IL-1α), which can control activation of IL-6 and IL-8 via amplification of C/EBPβ activation. Interestingly, while 6-shogaol is known to have strong anti-inflammatory properties, it did not display senomorphic effects in this study. Therefore, the anti-inflammatory impacts of 6-shogaol may not translate into senomorphic effects on senescent cells. This notion was further supported in our study suggesting that the senomorphic effect of gingerenone A and D+Q occurred through different mechanisms (FIGS. 12A, 12B).

Treatment with gingerenone A did not increase p53 levels in proliferating or senescent cells, but it reduced the expression of Bcl-XL in senescent cells, resulting in an increase in caspase-3. This result strongly suggests that gingerenone A operates through caspase-3 cleavage and independently of p53 activity.

The anti-inflammatory effects of gingerenone A observed are consistent with its senolytic/senomorphic effects due to the association between senescence and chronic inflammation. The results demonstrate that gingerenone A plays a role in inflammation and immune system regulation and has been identified as a novel senolytic/senomorphic through caspase-3 cleavage.

Example 4

Pharmacokinetic Study

Figure 14:
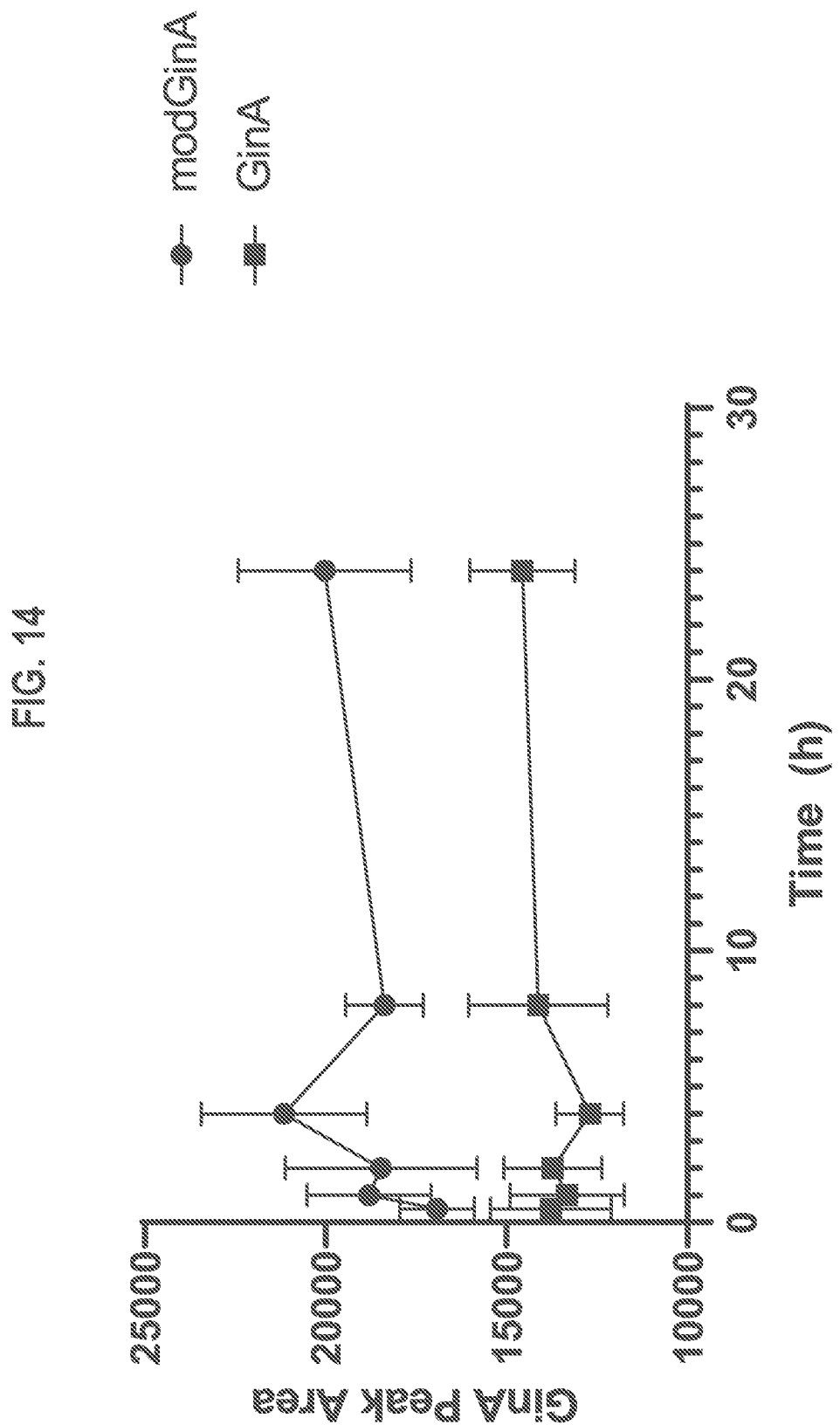
FIG. 14 shows the relative changes (peak area) in circulating gingerenone A plasma levels in C57BL/6J male mice receiving a p.o. administration of 10 mg/kg modGinA (a 1:1 mixture of DHA-GinA and EPA-GinA) (circles) or GinA (gingerenone A) (squares).

A preliminary pharmacokinetic study was conducted following a single oral administration of 10 mg/kg of gingerenone A (GinA, Aobius, Inc., Gloucester, MA; >95% purity by HPLC) alone and modGinA (a 1:1 mixture of DHA-GinA and EPA-GinA (>95% purity by NMR)) on C57BLK/6J male mice (FIG. 14). The peak areas in circulating gingerenone A levels were measured as described above in the Methods section. Modified gingerenone A was synthesized to increase bioavailability of gingerenone A, and that the data in FIG. 14 suggests that the AUC of modGinA was greater than the AUC for GinA.

Figure 15A:
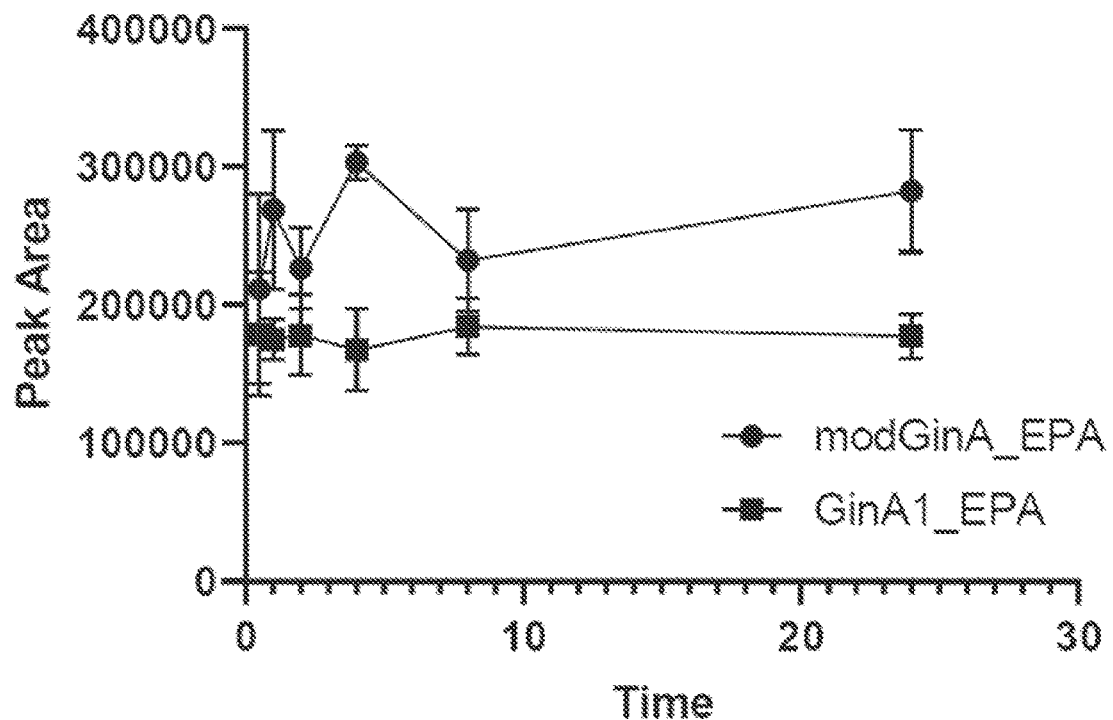
FIGS. 15A and 15B show the circulating levels of EPA (FIG. 15A) and DHA (FIG. 15B) in the mice of FIG. 14.
Figure 15B:
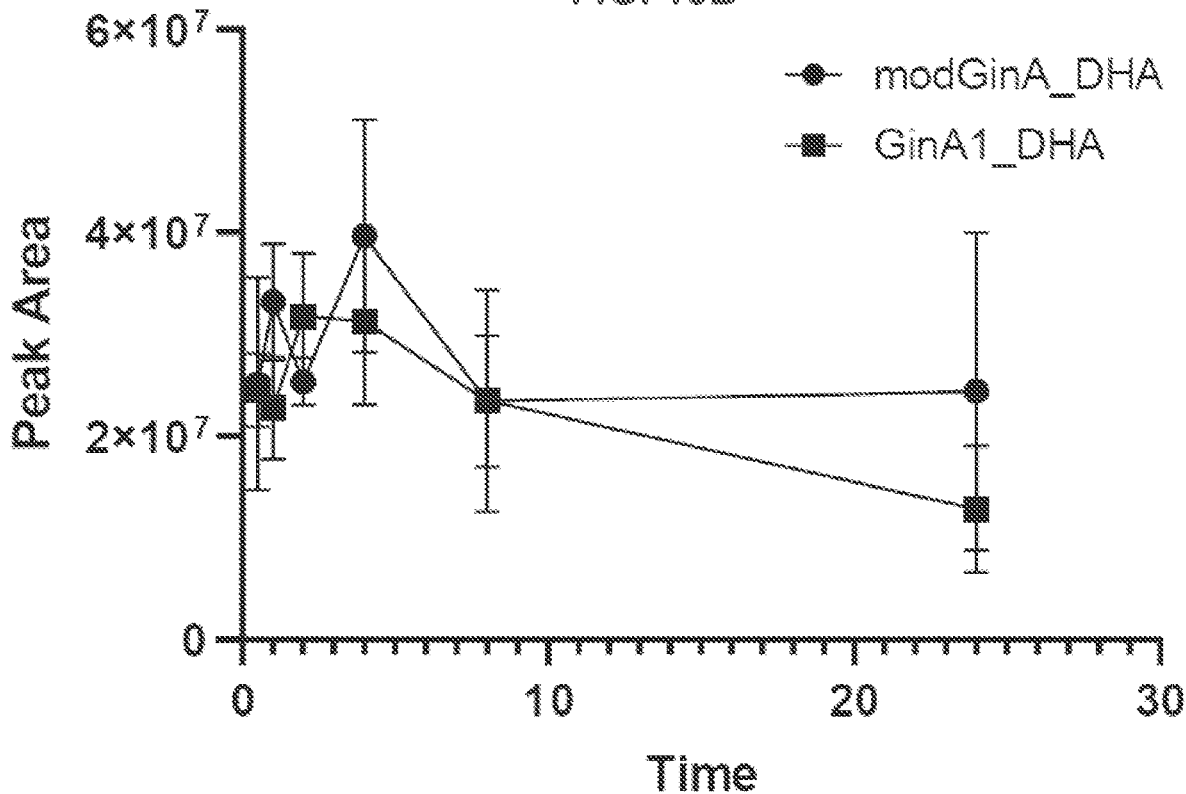

Circulating levels of EPA (FIG. 15A) and DHA (FIG. 15B) were also measured. The modGinA resulted in increased circulating levels of EPA relative to baseline (FIG. 15A).

Example 5

Synthesis of Lys-Gin A-DHA and Lys-Gin A-EPA

Figure 16A:
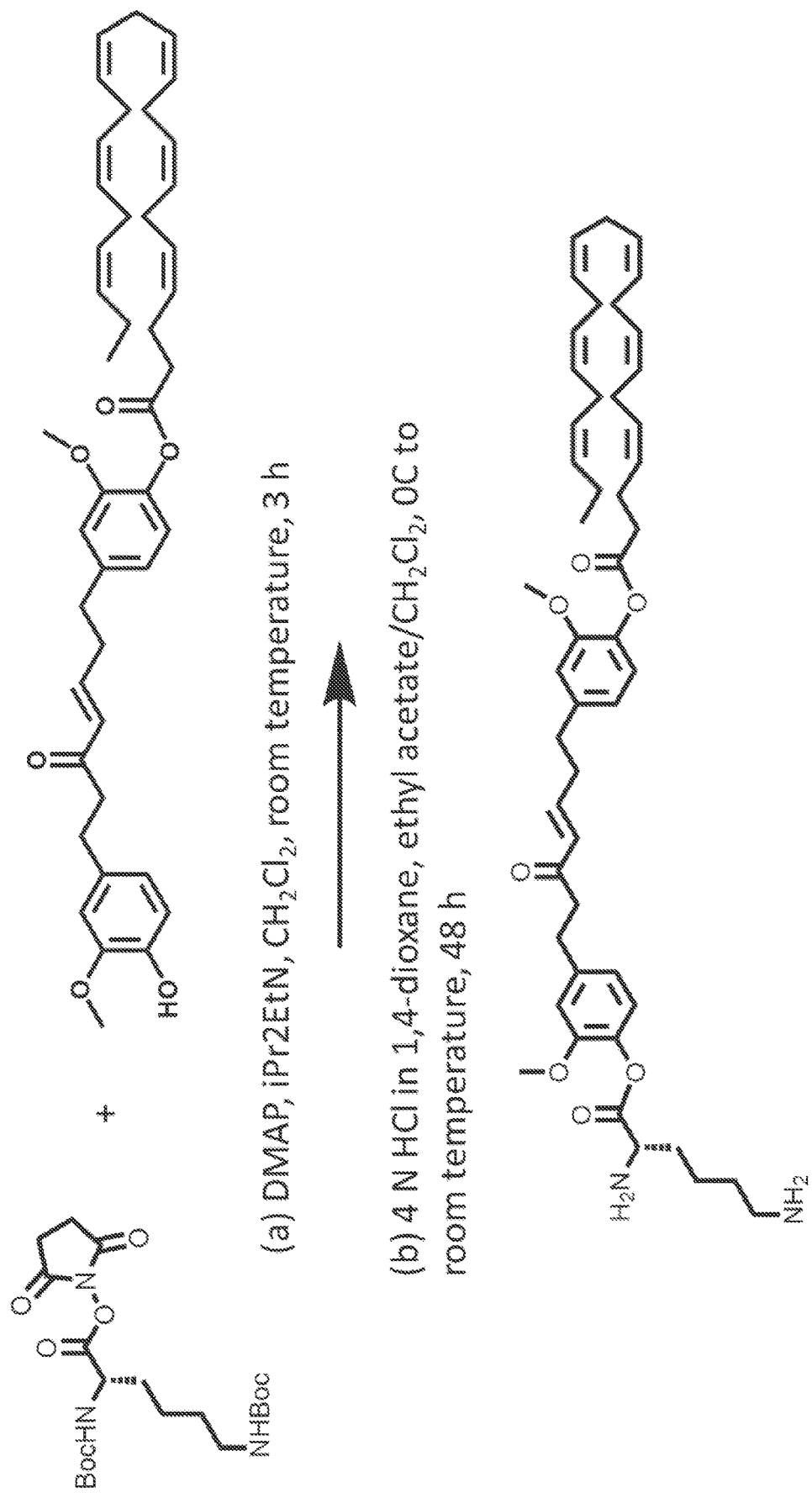
FIGS. 16A and 16B show exemplary syntheses of a prodrug comprising an amino acid moiety (lysine) and either DHA (FIG. 16A) or EPA (FIG. 16B).
Figure 16B:
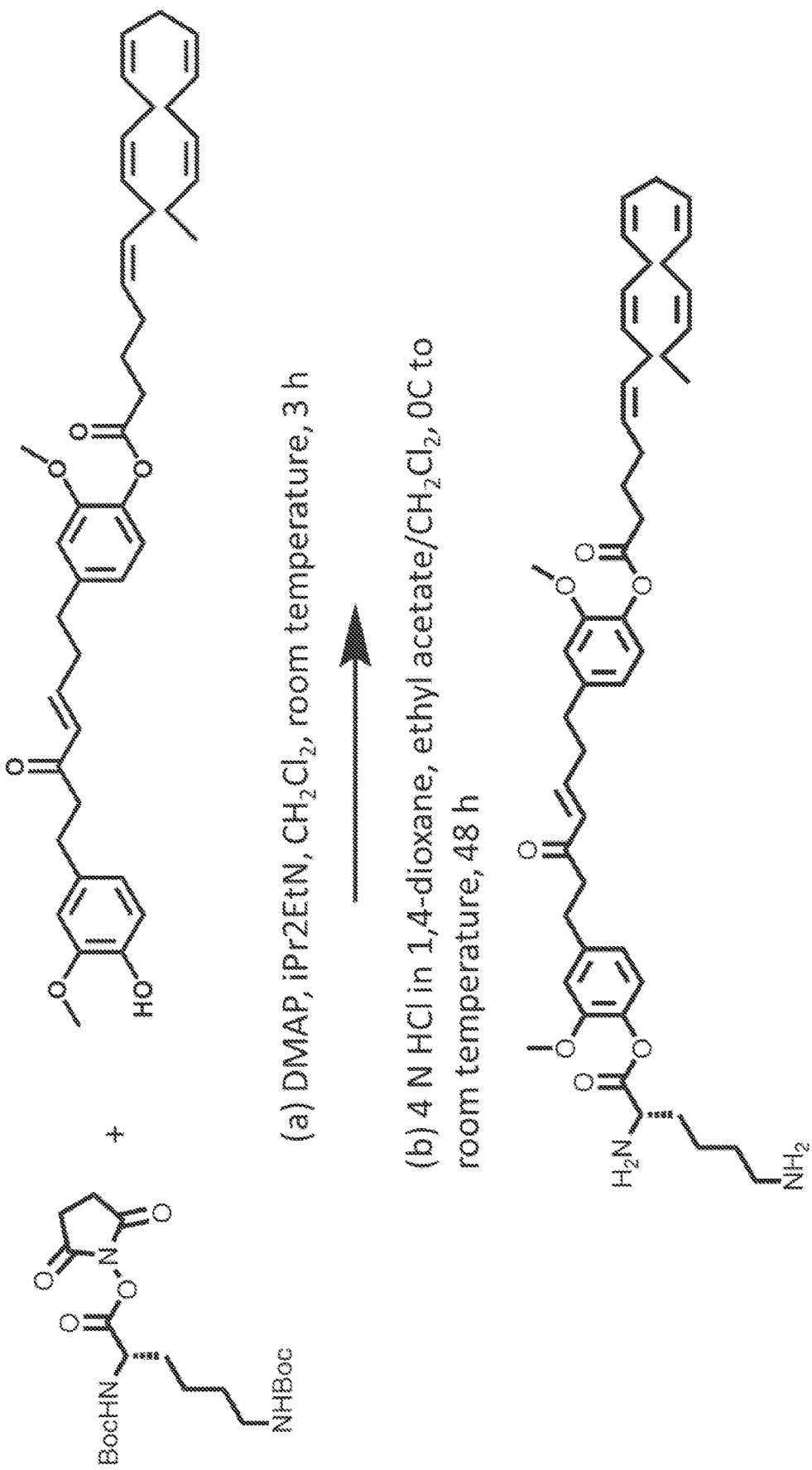

FIGS. 16A and 16B show exemplary syntheses of a gingerenone A prodrug comprising an amino acid moiety (lysine) and either DHA (FIG. 16A) or EPA (FIG. 16B). To a solution of Gin A DHA ester (10 mg) in dichloromethane (5 mL) is added diisopropylethylamine (3 equiv.) and 4-dimethylaminopyridine (0.2 equiv.), followed by Boc-Lys (Boc)-OSu (3 equiv.; dioxopyrrolidin-1-yl 2,6-bis((tert-butoxycarbonyl)amino)hexanoate (2,5-dioxopyrrolidin-1-yl) (2S)-2,6-bis[(2-methylpropan-2-yl)oxycarbonylamino] hexanoate). The mixture is stirred for 3 hours at room temperature, then it is purified by flash chromatography. The amines are deprotected in 50/50 ethyl acetate/dichloromethane by adding 4N HCl in dioxane at 0° C. and then allowing the reaction to reach room temperature. The reaction is stopped by carefully adding saturated NaHCO$_3$ at 0° C. and then extracting with ethyl acetate. A similar synthesis is performed starting with Gin A EPA ester.

Example 6

Senotherapeutic Effects of DHA- and EPA-Gingerenone A

ModGinA (a 1:1 mixture of DHA-GinA and EPA-GinA) will be orally administered to C57BL/6J mice (18-22 months old, naturally aging mice) for up to 15 weeks to determine senotherapeutic effects. ModGinA also will be orally administered to chemotherapy (doxorubicin)-induced senescent mice (60 p16TdTom mice) for up to 15 weeks to determine senotherapeutic effects.

ModGinA will be administered prior to chemotherapy (doxorubicin) to determine whether the modGinA prevents development of the senescent model in 60 p16TdTom mice. Oral administration will start 10 days prior to doxorubicin administration and continue for 20 days post-inoculation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a structure according to Formula I, or a stereoisomer, tautomer, or a pharmaceutically acceptable salt thereof:

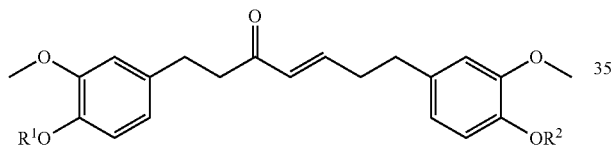

(I)

wherein one of $R^1$ and $R^2$ is —C(O)—R or H, and the other of $R^1$ and $R^2$ is —C(O)—R or —C(O)OH, where each R independently is $R^A$ or

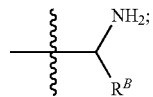

$R^A$ is $C_{18}$-$C_{22}$ alkenyl; and
$R^B$ is an amino acid side chain.

2. The compound of claim 1, wherein:
$R^1$ and $R^2$ are —C(O)—$R^A$ where each $R^A$ independently is $C_{18}$-$C_{22}$ alkenyl; or
one of $R^1$ and $R^2$ is —C(O)—$R^A$ and the other of $R^1$ and $R^2$ is

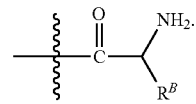

3. The compound of claim 1, wherein $R^A$ comprises two or more double bonds.

4. The compound of claim 1, wherein $R^B$ is —(CH$_2$)$_4$NH$_2$, —CH$_3$, —CH(CH$_3$)$_2$, —CH(CH$_3$) CH$_2$CH$_3$, —CH$_2$CH(CH$_3$)$_2$, —(CH$_2$)$_2$SCH$_3$, —CH$_2$OH, —CH(OH) CH$_3$, —CH$_2$C(O)NH$_2$, —(CH$_2$)$_2$C(O)NH$_2$, —CH$_2$SH, —CH$_2$NH$_2$, —(CH$_2$)$_3$N(H)C(=NH) NH$_2$, —CH$_2$COOH, —(CH$_2$)$_2$COOH,

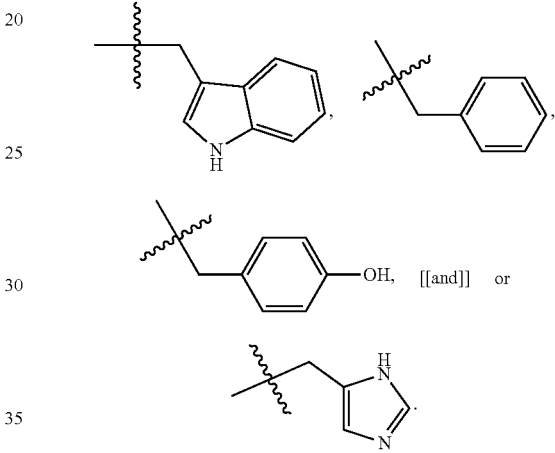

5. The compound of claim 1, wherein $R^1$ and $R^2$ independently are —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$.

6. The compound of claim 1, wherein:
one of $R^1$ and $R^2$ is

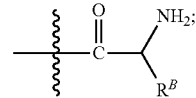

and
the other of $R^1$ and $R^2$ is —C(O)—(CH$_2$)$_3$—(CH=CH—CH$_2$)$_5$—CH$_3$ or —C(O)—(CH$_2$)$_2$—(CH=CH—CH$_2$)$_6$—CH$_3$.

7. The compound of claim 1, wherein the compound is:

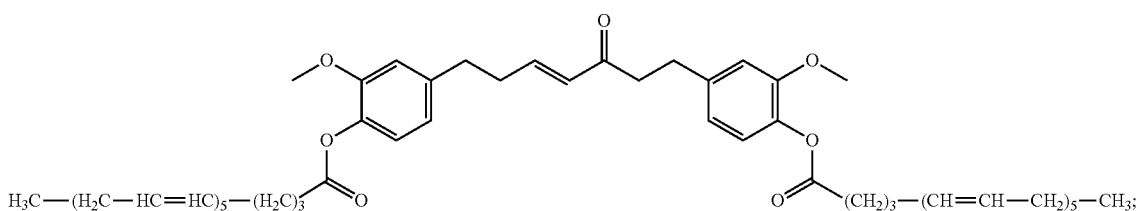

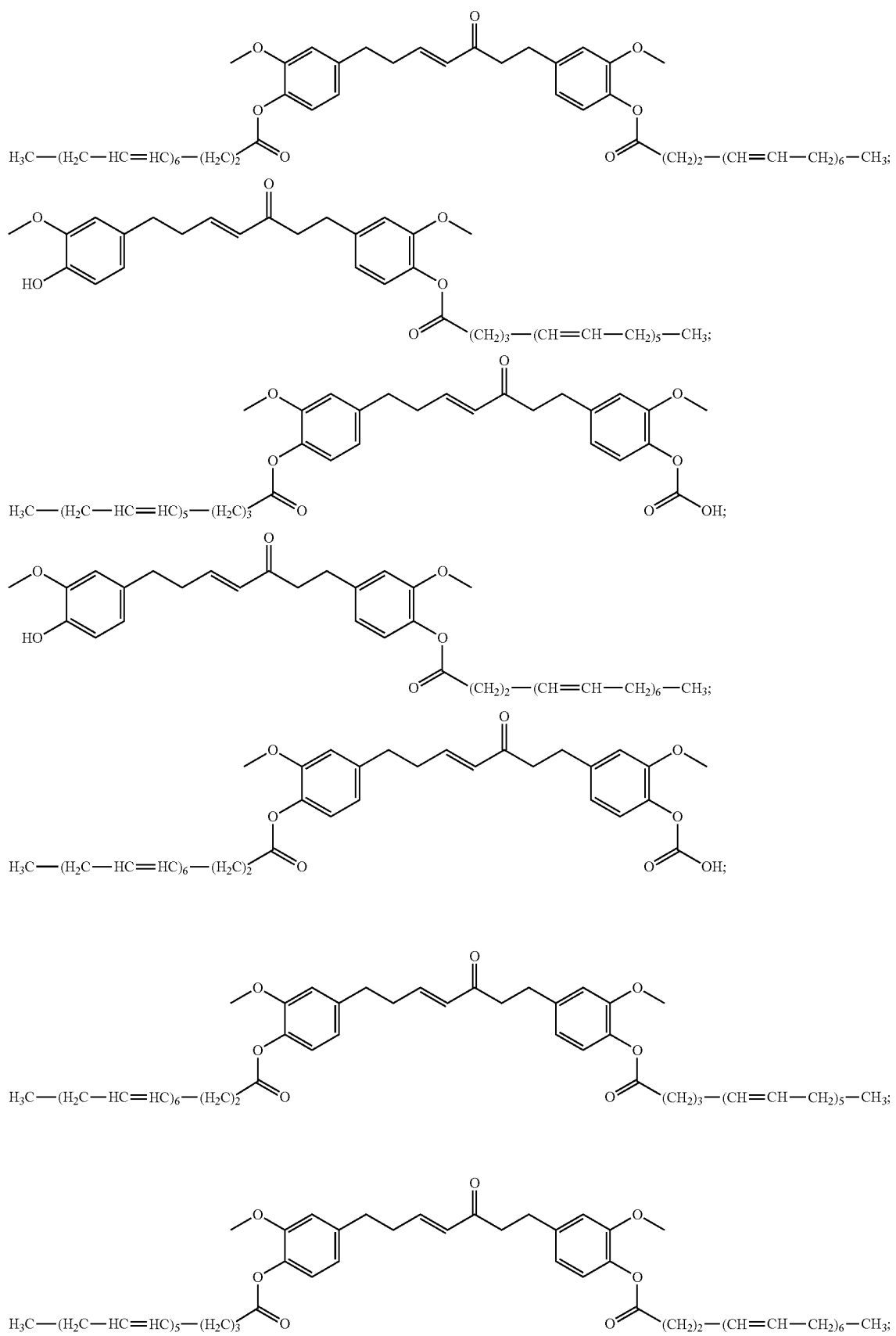

-continued
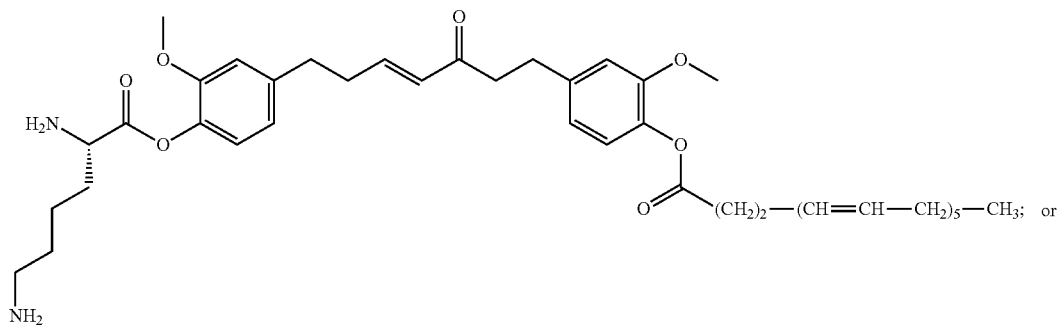
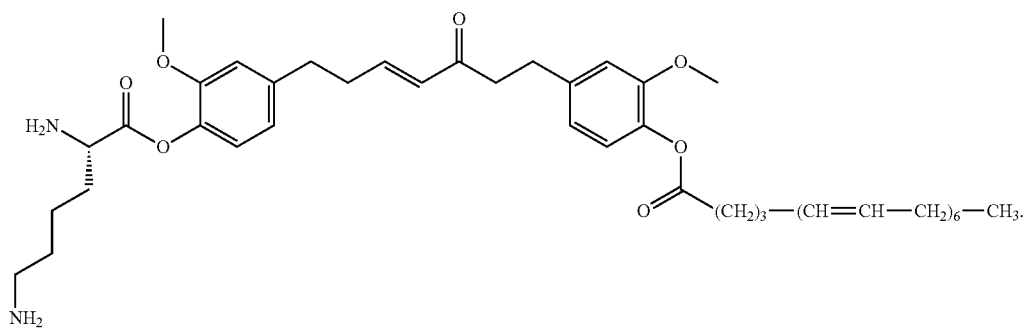
8. A pharmaceutical composition comprising:
a compound according to claim 1; and
a pharmaceutically acceptable carrier.
9. A method of inhibiting senescence, comprising contacting a senescent cell with an effective amount of a compound selected from the following
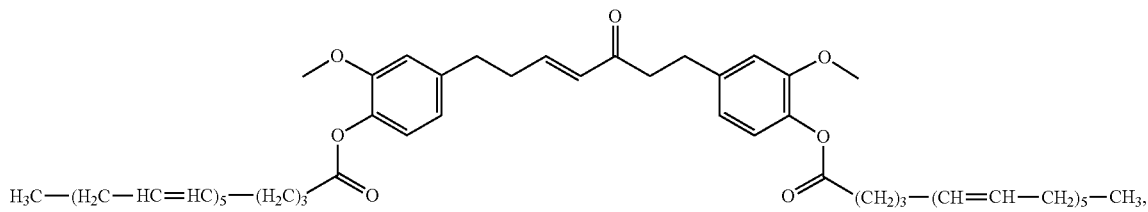
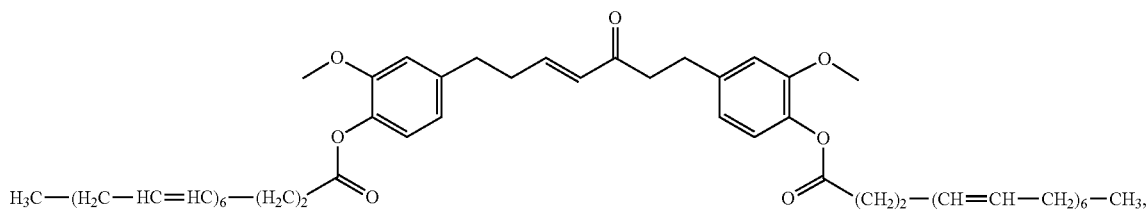
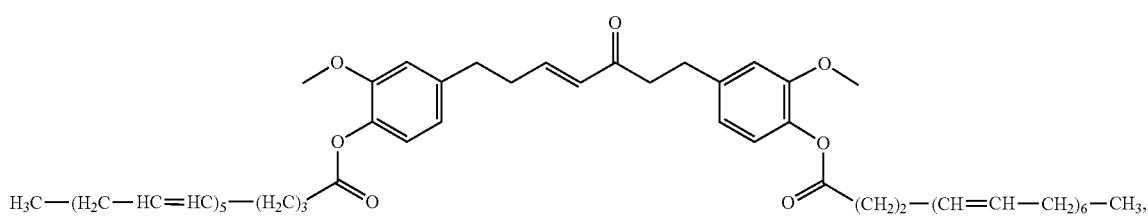

or a pharmaceutical composition comprising any one of the compound above and a pharmaceutically acceptable carrier.

10. The method of claim 9, wherein inhibiting senescence comprises killing the senescent cell, activating caspase-3 in the senescent cell, or a combination thereof.

11. The method of claim 9, wherein contacting is performed in vivo and the compound subsequently is cleaved in vivo to provide gingerenone A, $R^1OH$, and $R^2OH$.

12. The method of claim 9, wherein administering to the subject the therapeutically effective amount of the compound selectively kills senescent cells in the subject, activates caspase-3 in senescent cells in the subject, reduces secretion of interleukin-6 (IL-6) in the subject, reduces secretion of chemokine (C—C motif) ligand 2 (CCL2) in the subject, reduces secretion of interferon gamma-induced protein 10 (IP-10) in the subject, increases a level of interleukin-10 (IL-10) in the subject, increases a level of interleukin-13 (IL-13) in the subject, increases circulating levels of eicosapentaenoic acid in the subject, increases circulating levels of docosahexaenoic acid in the subject, increases circulating levels of 17-hydroxydocosahexanoic acid in the subject, increases circulating levels of an amino acid in the subject, reduces neuroinflammation in the subject, reduces frequency of physical pain in the subject, reduces intensity of physical pain in the subject, or any combination thereof.

13. The method of claim 9, wherein the compound or pharmaceutical composition is administered via an oral, parenteral, intramuscular, subcutaneous, topical, sublingual, intraocular, intranasal, inhalation, intrarectal, or intra-aural route.

* * * * *